US006816743B2

(12) United States Patent
Moreno et al.

(10) Patent No.: US 6,816,743 B2
(45) Date of Patent: Nov. 9, 2004

(54) METHODS AND APPARATUS FOR IN VIVO IDENTIFICATION AND CHARACTERIZATION OF VULNERABLE ATHEROSCLEROTIC PLAQUES

(75) Inventors: Pedro Moreno, Lexington, KY (US); Robert A. Lodder, Nicholasville, KY (US); William O'Connor, Lexington, KY (US); James E. Muller, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 352 days.

(21) Appl. No.: 09/768,920

(22) Filed: Jan. 24, 2001

(65) Prior Publication Data

US 2001/0047137 A1 Nov. 29, 2001

Related U.S. Application Data

(63) Continuation of application No. 09/169,621, filed on Oct. 8, 1998, now abandoned.

(51) Int. Cl.[7] .................................................. A61B 6/00
(52) U.S. Cl. ....................... 600/473; 600/476; 600/478; 600/479; 382/128; 382/130
(58) Field of Search ................................ 600/473, 476, 600/478, 479, 477, 306; 250/338.1, 339.01, 339.05, 339.11, 340, 341.1, 341.8; 382/128, 130

(56) References Cited

U.S. PATENT DOCUMENTS

| 4,240,692 A | 12/1980 | Winston | 350/96.1 |
| 4,378,159 A | 3/1983 | Galbraith | 356/237 |
| 4,515,165 A | 5/1985 | Carroll | 128/664 |
| 4,622,974 A | 11/1986 | Coleman et al. | 128/634 |

(List continued on next page.)

FOREIGN PATENT DOCUMENTS

| EP | 0 467 459 A2 | 1/1992 |
| EP | 0467 459 A3 | 1/1992 |
| SU | 649410 | 2/1979 |

OTHER PUBLICATIONS

Lodder, Robert A. et al. "Assessment of the Feasibility of Determination of Cholesterol and Other Blood Constituents by Near–Infrared Reflectance Analysis" The University of Georgia and International Business Machines Corporation, 1992.

Primary Examiner—Marvin M. Lateef
Assistant Examiner—Jeoyuh Lin
(74) Attorney, Agent, or Firm—Fish & Richardson P.C.

(57) ABSTRACT

Methods and apparatus for analyzing the chemical composition of vulnerable plaques with an intravascular catheter having a near-infrared light source, a fiber-optic probe, a mechanism for directing the light from the light source into a blood vessel, and detectors for detecting light reflected or scattered by the tissue. The light source may be a tunable laser, and may transmit an incident beam having a wavelength ranging from 1400 to 4100 nm. A computer may be included to receive and process the spectral data in the analysis of the vulnerable plaques. A catheter system may be configured to provide near-IR spectrometric imaging of arteries to non-destructively locate and determine lipid pool and fibrous cap size and composition. Additionally, mediators and cellular components may be also determined that are typically associated with vulnerable plaques which have an increased risk of rupture. The lipid pool, fibrous cap, and inflammatory response may serve as an in vivo marker for vulnerable atherosclerotic plaques. Methods are further provided for prospectively identifying and characterizing vulnerable plaques which may include the steps of focusing near-IR light onto a blood vessel wall; detecting the scattered light in the region; and analyzing the resulting spectra across the full preselected wavelength range, particularly in the ranges that include identifying peaks for vulnerable plaque constituents.

15 Claims, 9 Drawing Sheets

U.S. PATENT DOCUMENTS

| | | |
|---|---|---|
| 4,718,417 A | 1/1988 | Kittrell et al. ............ 128/303.1 |
| 4,799,754 A | 1/1989 | Goldenberg ............. 350/96.18 |
| 4,803,992 A | 2/1989 | Lemelson ................... 128/634 |
| 4,975,581 A | 12/1990 | Robinson et al. ........... 250/339 |
| 5,088,493 A | 2/1992 | Giannini et al. ............ 128/633 |
| 5,106,387 A | 4/1992 | Kittrell et al. ................ 606/15 |
| 5,197,470 A * | 3/1993 | Helfer et al. ............... 600/342 |
| 5,293,872 A * | 3/1994 | Alfano et al. ................ 600/475 |
| 5,441,053 A | 8/1995 | Lodder et al. .............. 128/664 |
| 5,813,403 A | 9/1998 | Soller et al. ................. 600/310 |
| 5,944,653 A | 8/1999 | Bonnell et al. ............. 600/109 |
| 5,999,844 A | 12/1999 | Gombrich et al. .......... 600/476 |
| 6,272,376 B1 * | 8/2001 | Marcu et al. ............... 600/477 |
| 2002/0156380 A1 * | 10/2002 | Feld et al. .................. 600/473 |

\* cited by examiner

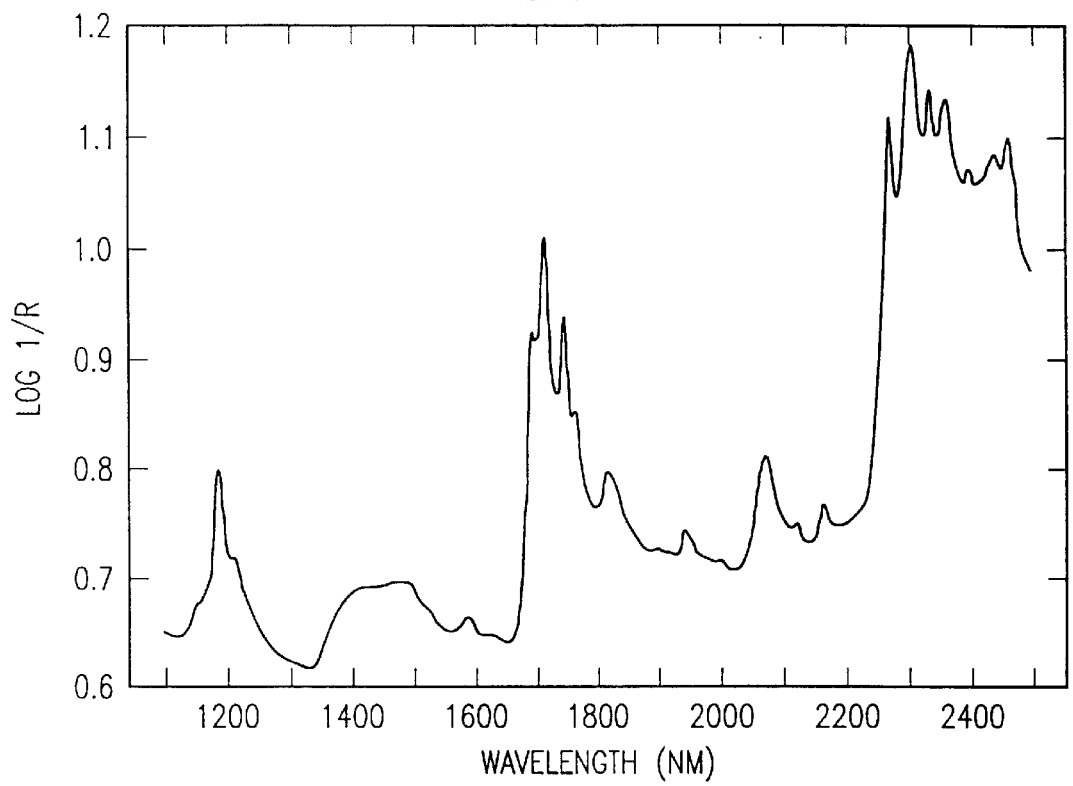
FIG. 1 CRYSTALLINE CHOLESTEROL
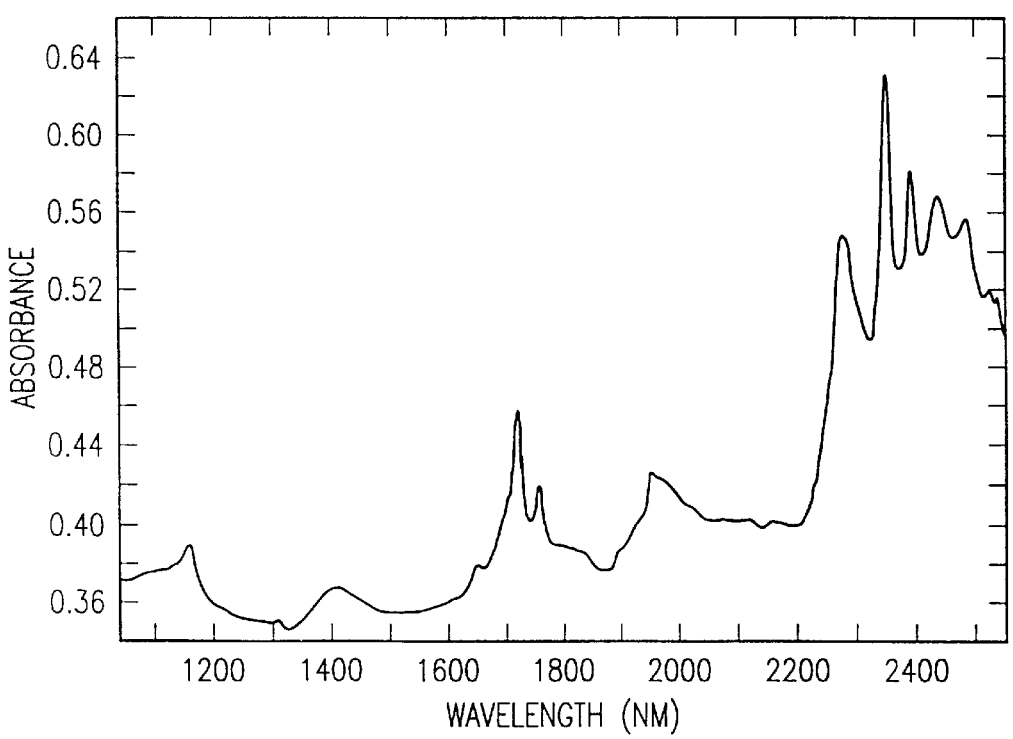
FIG. 2 LYSOPHOSPHOR CHOLESTEROL

FIG. 11

1) 31 SAMPLES FROM A SINGLE AORTA WERE ANALYZED BY HISTOLOGY FOR GRUEL AND THIN CAP.
2) 15 SAMPLES WERE USED AS A TRAINING SET FOR NEAR IR ANALYSIS.
3) THE REMAINING 16 WERE ANALYZED BLINDLY BY DR. LODDER FOR PRESENCE OR ABSENCE OF GRUEL AND A THIN CAP.
4) RESULTS:

GRUEL IN PLAQUE
BY HISTOLOGY

|  | YES | NO |
|---|---|---|
| BY NEAR IR YES | 10 | |
| BY NEAR IR NO | | 6 |

THIN FIBROUS CAP
BY HISTOLOGY

|  | YES | NO |
|---|---|---|
| BY NEAR IR YES | 6 | |
| BY NEAR IR NO | | 10 |

METHODS AND APPARATUS FOR IN VIVO IDENTIFICATION AND CHARACTERIZATION OF VULNERABLE ATHEROSCLEROTIC PLAQUES

This application is a continuation (and claims the benefit of priority under 35 USC 120) of U.S. application Ser. No. 09/169,621, filed Oct. 8, 1998 now abandoned. The disclosure of the prior application is considered part of (and incorporated by reference in) the disclosure of this application.

FIELD OF THE INVENTION

The present invention relates to the field of atherosclerosis intervention. More specifically, the invention relates to near-infrared imaging for in vivo identification and characterization of tissue including vulnerable atherosclerotic plaques.

BACKGROUND OF THE INVENTION

Over the past two decades, valuable studies have been conducted using new intracoronary technologies to characterize coronary lesions in living patients. These new technologies include angioscopy, ultrasound, and atherectomy. Studies based upon these approaches have further added to the knowledge gained from post-mortem studies. While much has been learned during post-mortem studies, by definition, these investigations cannot provide prospective data. Furthermore, the procedures used in living patients, cannot usually provide detailed information on the chemical composition of the diseased tissue. A significant amount of relevant information, however, has been derived over the years through various studies on coronary lesions.

The characterization of lesions causing acute coronary syndromes has been advanced significantly by post-mortem observations. It was earlier observed that in human autopsy specimens of thrombosed coronary arterial segments, the thrombus was situated at the site of a plaque where an intimal fracture allowed the exposure of soft, abscess-like lipoid material into the lumen of the blood vessel (Constantinides P, Plaque fissures in human coronary thrombosis, J Atheroscler Res 1966; 6:1–17 (cited references are incorporated herein by reference)). Subsequently, it was shown that coronary thrombi responsible for fatal myocardial infarction were almost exclusively found at the site of disrupted plaques (Davies M J, Thomas A C, Thrombosis and acute coronary artery lesions in sudden cardiac ischemic death, N Engl J Med 1984; 310:1137–40; Davies M J, A macro and micro view of coronary vascular insult in ischemic heart disease, Cir 1990; 82(3):38–46; Falk E, Plaque rupture with severe pre existing stenosis precipitating coronary thrombosis: Characteristics of coronary atherosclerotic plaques underlying fatal occlusive thrombi, Br Heart 1983; 50:127–34). The lipid content of human aortic plaques displaying ulceration and thrombosis was observed to be greater than that of non-disrupted plaques. Similarly, in patients dying of acute myocardial infarction, previous research revealed that while culprit lesion morphology in myocardial infarction is heterogeneous with respect to plaque architecture and cellular composition (van der Wal A C, Becker A E, van der Loos C M, Das P K, Site of intimal rupture or erosion of thrombosed coronary atherosclerotic plaques is characterized by an inflammatory process irrespective of the dominant plaque morphology, Circulation 1994; 89:36–44), the immediate site of plaque rupture is marked by an inflammatory process. An incidence of plaque disruption of about 83% has been also reported, similar to that of infarction, in patients with unstable angina. Additional reports noted the occurrence of coronary thrombosis at sites that do not show typical signs of plaque rupture (Burke A P, Farb A, Malcom G T, Liang Y-H, Smialek J, Virmani R, Coronary risk factors and plaque morphology in men with coronary disease who died suddenly, N Engl J Med 1997; 336:1276–82). These have been termed sites of erosion, and it is estimated that they are responsible for approximately 30% of coronary thrombi, with plaque rupture accounting for the remainder. There is a frequent occurrence in these studies of lipid-rich plaques with thin caps, both ruptured and non-ruptured, as incidental findings in patients dying of other coronary lesions, or non-cardiac causes (Falk E, Shah P K, Fuster V, Coronary plaque disruption, Circ. 1995; 92:657–71). It has also been observed that approximately 80% of patients dying suddenly had such lesions in addition to their culprit lesions (Farb A, Burke A P, Tang A L et al, Coronary plaque erosion without rupture into a lipid core: A frequent cause of coronary thrombosis in sudden coronary death, Circulation 1996; 93:1354–63). Although many post-mortem studies have yielded valuable information, there are several important limitations to their use. Because of possible selection bias, the findings derived from autopsy studies can be generalized with certainty only to those who die of acute coronary syndromes. It is quite possible that the prevalence, nature, and degree of plaque disruption and/or associated thrombosis of culprit lesions, is different in those surviving the disease. Results from autopsy studies suggest nonetheless that most acute lesions arise from a plaque that includes a lipid pool, a thin cap, and macrophage infiltration. While prospective studies have been limited, these histologic features may be considered to represent a "vulnerable plaque", a term first defined by Muller et al (Muller J E et al, Triggers, Acute Risk Factors and Vulnerable Plaques: The Lexicon of a New Frontier, JACC 1994; 23(3) 809–13). This type of plaque refers to its functional property of having an increased likelihood of rupture, and may include more than one histologic type.

The coronary angiogram is considered a primary source of information for living patients with lesions that cause acute coronary syndromes. Recently, retrospective analysis of coronary angiograms in patients who subsequently developed unstable angina and myocardial infarction demonstrated that many culprit lesions originate from plaques previously causing less than 50% stenosis (Ambrose J A, Tannenbaum M A, Alexopoulos D et al, Angiographic progression of coronary artery disease and the development of myocardial infarction, J Am Coll Cardiol 1988; 12, 56-62; Ambrose J A, Winters S L, Arora R R et al, Angiographic evolution of coronary artery morphology in unstable angina, J Am Coll Cardiol 1986; 5,472–8; Nobuyoshi M, Tanaka M, Nosaka H et al, Progression of coronary atherosclerosis: is coronary spasm related to progression? J Am Coll Cardiol 1991; 18, 904–10; Little W C, Downes T R, Applegate R J, The underlying coronary lesion in myocardial infarction: implications for coronary angiography, Clin Cardiol 1991; 14, 868–74). The residual stenosis, after successful thrombolytic therapy, was found to be of only moderate severity in many cases, supporting the concept that occlusive thrombus frequently develops at coronary sites without prior severe stenosis (Kereiakes D J, Topol E J, Sea G, Myocardial infarction with minimal coronary atherosclerosis in the era of thrombolytic reperfusion, J Am Coll Cardiol 1991; 17, 304–12; Brown G G, Gallary C A, Badger R S et al, Incomplete lysis of thrombus in the moderate underlying atherosclerotic lesion during intracoronary infusion of streptokinase for acute myocardial infarction, Circulation 1986; 73, 653–61). Despite these advances, the use of coronary angiography to study coronary atherosclerotic lesions in living patients has severe limitations including its inability to provide information about the sub-surface features of the plaque. The relatively low sensitivity and specificity of a plaque's geometric surface features to predict subsequent occlusion indicate that other plaque-related characteristics (i.e., plaque composition), not detectable by angiography, may be more important in the determination of plaque vulnerability (Taeymans Y, Theroux P, Lesperance J, Waters D, Quantitative angiographic morphology of the coronary artery lesions at risk of thrombotic occlusion, Circulation 1992; 85, 78–85).

The development of angioscopic imaging devices for the coronary arteries also provided a valuable opportunity to define the surface features of lesions which cause unstable angina and acute coronary syndromes. Angioscopic imaging devices were used percutaneously to obtain a clear view, with magnification, of the inner surface of the coronary lumen in patients undergoing catheterization. Normal segments of coronary arteries in living patients were observed to be white and smooth, while disrupted atherosclerotic plaques causing disease were elevated and, in many cases, yellow and/or red in color (Mizuno K, Miyamoto A, Satomura K et al, Angioscopic coronary macromorphology in patients with acute coronary disorders, Lancet 1991; 337, 809–12). Imaging of the site of percutaneous transluminal coronary angioplasty (PTCA) also permitted identification of the mechanism of abrupt closure (Sassower M A, Abela G S, Koch J M et al, Angioscopic evaluation of peri-procedural and post-procedural abrupt closure following percutaneous coronary angioplasty, Am Heart J 1993). A study using angioscopy demonstrated that patients with "glistening yellow" plaques had a 68% incident rate within the subsequent year of unstable angina or myocardial infarction, as opposed to a 4% in those without such lesions (Uchida et al, Prediction of acute coronary syndromes by percutaneous coronary angioscopy in patients with stable angina, Amer Heart J 1995, 130 (2): 195–203). Despite the obvious advantages of imaging the interior of a coronary artery, the angioscope can only generally provide information about the shape and color of the interior surface of the blood vessel. The technique also requires a period of coronary occlusion and an experienced team for safe performance. The interpretation of findings with terms such as "glistening yellow" are particularly subjective and may provide inconsistent results.

Intracoronary ultrasound devices have been also used to characterize coronary lesions. It is possible to identify certain characteristics of these lesions beneath their intimal surface. The ability of intravascular coronary ultrasound (ICUS) to identify tissue characteristics of lesions has been established in in vitro studies with histologic correlation (Tobis J M, Mahon D, Moriuchi M et al, Intravascular ultrasonic imaging, Tex Heart Inst J 1990; 17, 181–9; Tobis J M, Mallery J, Mahon Dea, Intravascular ultrasound imaging of human coronary arteries in vivo: Analysis of tissue characterizations with comparison to in vitro histologic specimens, Circ. 1991; 83, 913–26). Fibrous plaques produce bright images with echo-free shadowing. Plaques with extracellular lipid or necrotic material displayed minimal reflectivity typically appearing in the form of hypoechoic areas, but differentiation from thrombus is quite often difficult. Such correlation studies have led to widespread use of the terms "hard" or "soft" to characterize lesions based on these ultrasonic images (Hodgson J M, Reddy K G, Suneja R, Nair R N, Lesnefsky E J, Sheehan H M, Intracoronary ultrasound imaging: correlation of plaque morphology with angiography, clinical syndrome, and procedural results in patients undergoing coronary angioplasty, J Am Coll Cardiol 1993; 21, 35–44; Nissen S E, Gurley J C, Booth D C, McClure R R, Berk M R, DeMaria A N, Spectrum of intravascular ultrasound findings in atherosclerosis: wall morphology and lumen shape in CAD patients, J Am Coll Cardiol 1991; 93; Nissen S E, Gurley J C, Grines C L, Booth D C, McClure R, Berk M, Intravascular ultrasound assessment of lumen size and wall morphology in normal subjects and patients with coronary artery disease. Circ. 1991; 84, 1087–99). Unfortunately, the sensitivity and specificity of ICUS to identify particular components of a lesion, including lipid-rich regions with thin caps, is limited by the resolution of ICUS technology, and its further inability to identify chemical composition of subject tissue.

The performance of atherectomy procedures further provided significant information relating to coronary lesions. For example, in a study of atherectomy specimens in living patients with stable and unstable coronary syndromes (Moreno P R, Falk E, Palacios I F, Newell J B, Fuster V, Fallon J T, Macrophage infiltration in acute coronary syndromes: Implications for plaque rupture, Circulation 1994; 90:775–8), it was shown that macrophage-rich areas are more frequently found in patients with unstable angina and non-Q wave myocardial infarction, and are a marker of unstable atherosclerotic plaques. More recently, macrophages have been identified as a major source of tissue factor establishing a cell-mediated thrombogenicity in unstable atherosclerotic plaques (Moreno P R, Bernardi V H, Lopez-Cueller J et al, Macrophages, smooth muscle cells and tissue factor in unstable angina: Implications for cell-mediated thrombogenicity in acute coronary syndromes, Circulation 1996; 94:3090–7). There are however several limitations to the use of atherectomy specimens to study vulnerable coronary plaques. The technique is no longer in frequent use for clinical purposes, and it is anticipated that many plaques causing disease will not be stenotic, and hence cannot be sampled by atherectomy performed for clinical indications. Sampling errors may also occur if only the superficial aspect of the plaque is retrieved which obscure anatomic relationships with the rest of the plaque.

Other techniques for analyzing coronary lesions have been also proposed. Recent approaches for identification of vulnerable plaque, for example, include thermography, ultra-fast CT, magnetic resonance imaging (MRI) and optical coherence tomography (OCT) (Brezinski M E, Tearney G J, Bouma B E et al, Optical coherence tomography for optical biopsy. Circulation 1996; 93:1206–13; Brezinski M E, Tearney G J, Weissman N J et al, Assessing atherosclerotic plaque morphology: Comparison of optical coherence tomography and high frequency intravascular ultrasound, Heart 1996; 77:397–403; Toussaint J-F, LaMuraglia GMSJF, Fuster V, Kantor H L, Magnetic resonance images lipid, fibrous, calcified, hemorrhagic, and thrombotic components of human atherosclerosis in vivo, Circ. 1996; 94:932-8). Each of these approaches exhibit some relative strengths and limitations. For example, thermography has not yet been validated in vivo, and ultrafast CT is an excellent way to detect calcium but other ions and compounds are not detected. MRI is generally not suited for imaging of the small, moving coronary arteries, as opposed to the relatively sizable carotids. OCT can provide images but has not yet been reported to obtain images through blood. The limitations of these techniques for analyzing arterial diseases preclude their useful and practical application for clinical purposes.

It has been generally observed that atherosclerosis, without associated thrombosis, is often an innocuous and asymptomatic disease. Many patients with atherosclerosis can be treated surgically or by drugs with high initial success, and often have a favorable long-term prognosis. The acute manifestation of atherosclerosis, commonly occurring as myocardial infarction, unstable angina, or sudden death, usually arises when thrombus develops. These serious events typically develop at the site of plaque fissure or rupture. A number of studies have demonstrated that plaque rupture plays a pivotal role in the pathophysiology (the physiology of abnormal states and the functional changes that accompany a particular syndrome or disease) of acute coronary syndromes. Recent research indicates that it is often not the severity of stenosis (a narrowing or constriction of the diameter of an artery by plaque volume) that determines a potential outcome. It is more often the type of stenosis, or the chemical composition of the plaque, and the extent of collateral growth which becomes a determining factor. The kind of plaque, determined by composition, consistency, vulnerability and thrombogenicity, varies greatly from patient to patient, even from plaque to plaque in different locations, and there is no simple relation among plaque kind, plaque volume or stenosis severity.

Near-IR spectrometry has been performed in a limited number of applications for analyzing and detecting the presence of known indicators associated with a particular disease or condition. For example, lipids have been examined with near-IR in vitro and in vivo in gerbil brains following experimentally induced stroke, and provided the identification of nine different saturated and unsaturated fatty acids found in the gerbil brain. The changes in water content related to edema and changes in proteins were also monitored non-invasively by near-IR spectrometry in these studies. Near-IR spectrometry has also been used to analyze HDL, LDL, and cholesterol in the blood vessels of rats, and has been performed with fiber-optic probes to determine fat content in meats commercially (Nagao A, Uozumi J, Iwamoto M, Yamazaki M, Determination of fat content in meats by near-infrared reflectance spectroscopy, Chem Abstr 1985; 219697r), and to determine total body lipids in humans non-invasively (Conway J, Norris K, Bodwell C, A new approach for the estimation of body composition: Infrared interactance, Amer J Clin Nutr 1984; 1123). In addition, near-IR imaging has been used in human stroke patients to analyze atherosclerotic plaque by identifying and locating oxidized lipoprotein spectral signatures. A near-IR imaging system and parallel vector supercomputer has been used with a fiber-optic probe to produce chemical maps of the intimal surface of living arteries. Spectrometric data collected at hundreds of near-IR wavelengths were assembled into color pictures of the lipoprotein and apolipoprotein composition of early atheromas using a vectorized 3-D cellular automaton-based algorithm that operates in parallel. The nonparametric mathematics developed to identify and quantify the constituents of each voxel in the artery wall avoided the matrix factorization that generates excess error in other pattern recognition methods, and permitted analysis in a wavelength space of over 1000 dimensions using fewer than 100 calibration samples. A surface feature resolution of 5.5 micrometers and depth resolution of 6.5 micrometers were achieved with the system. Controlling the apertures on fiber-optic probes permitted the three-dimensional relationships between sample components to be determined. Data from the fiber-optic probe confirmed the injury hypothesis of lesion formation and the differing roles of HDL and LDL in cholesterol transport. Additionally, near-IR spectrometry has been used trans-arterially on exposed carotid arteries in living patients undergoing endarterectomy. Images were obtained of fibrous cap, lipids, thrombus, ulceration and necrosis with an indium antimonide focal plane array video camera (Dempsey R J, Cassis L A, Davis D G, Lodder R A, Near-infrared Imaging and Spectroscopy in Stroke Research: Lipoprotein Distribution and Disease, Ann. N.Y. Acad. Sci. 1997; 820:149–69). It has been observed that near-IR spectral analysis has chemical imaging ability, and further provides useful information and detail relating to various internal body structures such as muscle, bone, and arteries (Van de Van M, French T, Fishkin J, Gratton F, Near-infrared imaging spectroscopy of mammalian tissue in the frequency domain. Biophys J 1991; 167a). Near-IR Raman spectroscopy has been also used recently to quantitatively analyze the lipid component of human atherosclerotic plaques (Weinmann et al, Quantitative analysis of cholesterol and cholesteryl esters in human atherosclerotic plaques using near-infrared Raman spectroscopy, Atherosclerosis 1998; 140(1), 81–8) and may provide vibrational information on chemical structures without penetration of more than a few microns of water or blood. While Raman spectroscopy may provide some analysis of plaque under certain test conditions, many technical difficulties including its inherent inefficiency prevent or limit its broad application in living patients through catheter-based systems. The performance of Raman spectroscopy through a catheter is also believed to be a time-consuming and inherently inefficient process that fails to provide accurate quantification of plaque constituents.

SUMMARY OF THE INVENTION

The present invention provides reliable methods and apparatus for detecting and analyzing the composition of vulnerable plaques in living tissue with near-infrared (IR) radiation. The invention, in a non-destructive manner, may provide early detection of vulnerable plaques before the onset of an acute syndrome. Near-IR spectroscopy, a variant of the procedure used to determine the chemical composition of extraterrestrial rock samples, may identify plaques with a lipid pool and thin cap in vivo. In accordance with the invention, this may be performed through a near-IR coronary catheter for identifying vulnerable plaques in the coronary arteries of living patients. The small risk to patients associated with near-IR imaging will be balanced against the possible benefits of improved risk-stratification and effective therapy.

Another object of the present invention is to provide a method and apparatus specifically adapted to identify vulnerable plaques to thereby allow physicians to prescribe appropriate drugs that are more likely to provide effective treatment. This is a particularly important consideration when it is realized that some of the drugs or devices prescribed to treat lesions may have serious side effects which may, in some instances, be avoided altogether. Still another object of the invention is to provide a method and apparatus wherein infrared radiation of a wavelength range from about 1400–4100 nm, and more preferably from about 1600–1800 nm, is sequentially focused onto selected arterial endothelium. The reflected or scattered infrared radiation may be then detected and analyzed at high speed in accordance with the invention to not only identify vulnerable plaques, but to also evaluate the progression of disease and effectiveness of treatment.

In accordance with the principles of the present invention, improved near-IR imaging apparatus may be provided for analyzing vulnerable plaques The apparatus may not be only utilized for in vitro analysis, but may also be advantageously utilized for in vivo analysis. The apparatus may comprise a light source for transmitting simultaneously and in parallel an incident beam of light of a wavelength range from approximately 1400 to 4100 nm, and more preferably within a "water window" such as from about 1600 to 1800 nm or around 2080 nm. A fiber-optic probe may be operatively connected to the light source, and a light directing or focusing mechanism may be mounted to the distal end of the probe. The focusing mechanism may comprise a compound parabolic concentrator (CPC) that may, for example, be formed from plastic and include a polished aluminum lining. The CPC is similar to those designed for use for solar power concentration. In particular, the CPC may be adapted to compress the incident beam from the transmitting fiber-optic onto a small spot on the tissue surface undergoing analysis. Additionally, the apparatus may include detectors such as lead sulfide detectors for detecting the scattered light from the artery surface or other tissue being analyzed. In an alternative embodiment, the light directing mechanism comprises an inverted, substantially conical reflector developed from both ellipsoids of rotation and paraboloids of rotation. This reflector may direct the incident beam from the transmitting optic fiber over the tissue undergoing analysis. Additionally, light reflected or scattered by the tissue is directed or focused into receiving optic fibers so as to allow for better detection and hence, chemical analysis of the tissue. The fiber-optic catheter may also comprise separate bundles of fibers to inject light into the vessel wall at one location, and detect light scattered through the plaque and vessel wall at another location. The light injection and detection ports may be placed in contact with the vessel wall using a balloon or other device during the measurement and therapeutic processes. A portion of the transmitting fibers may also be directed onto a reflectance standard at the catheter tip and returned to a detector module for use in absorbance ratios. The apparatus may further include suitably sized catheters and equipment for high speed parallel analyzing of the spectra reflected from the tissue, and producing color images thereof. Such equipment may, for example, include a computer such as a supercomputer used at the University of Kentucky, and appropriate software such as the copyrighted Bootstrap Error-Adjusted Single-Sample Technique (BEST) Algorithm software program developed by Robert A. Lodder. Further, the fiber-optic probe may be preferably adapted for introduction into a patient to thereby allow in vivo analysis of artery walls, or in particular, lesions which may characterized as vulnerable plaques. Additional information relating to these and other applications of the present invention may be further described in U.S. Pat. No. 5,441,053 (APPARATUS AND METHOD FOR MULTIPLE WAVELENGTH ANALYSIS OF TISSUE) which is incorporated by reference herein.

A further aspect of the present invention provides various methods of analyzing arterial lesions with near-IR spectroscopy for the existence of vulnerable plaque characteristics. The method may include the steps of focusing light on the tissue to be analyzed, and detecting light reflected by the tissue. The light being focused may have a wavelength ranging from approximately 1400 to 4100; and more preferably 1600 to 1800 nm. The method may further include a step of analyzing the spectra from the tissue and producing color images thereof. Advantageously, both the focusing and analyzing steps may be performed to allow high speed data acquisition and analysis. Specifically, light having a range of wavelengths from 1400 to 4100 nm, and more preferably from 1600 to 1800 nm, may be simultaneously focused in parallel at all locations being analyzed. The analysis of the reflected light may be also completed simultaneously and in parallel for all locations being analyzed over the same range of wavelengths. As all tissues absorb light at all these wavelengths, with different tissues absorbing only a little more at some wavelengths than others, this broad band parallel approach may be useful to reduce the risk of missing unusual tissue during study. Hence, the analysis may be more accurate and complete. When identifying peaks for particular lipids and cholesterol which are known to occur at certain ranges or water windows, the analysis may be modified in accordance with the invention to more readily detect and identify the existences of vulnerable plaques. Furthermore, as the focusing of near-IR radiation and analysis are performed in parallel, the complete study may still be completed in a sufficiently short time span to allow clinical utilization as with arterial angiography. In accordance with a further method of analyzing arterial endothelium in vivo utilizing a fiber-optic probe, the method may include the initial step of introducing the probe into an artery of a patient in combination with a coronary catheter. A Nd:YAG-pumped KTP/OPO tunable near-IR laser system may be utilized as a light source for the fiber-optic catheters and related methods disclosed herein. The BEST algorithm may be used to construct chemical-composition images of the intima of the aorta in test subjects in vivo.

It is another object of the invention to provide methods and apparatus using near-IR spectrometric imaging to non-destructively locate and identify pools of LDL cholesterol which may serve as an in vivo marker for vulnerable atherosclerotic plaques. Vulnerable plaques are thought to usually contain a sizable lipid pool containing LDL covered by a thin fibrous cap. Near-IR imaging spectrometry may be performed as prescribed herein to measure the size and the chemical composition of the fibrous cap and the lipid pool. An accurate measurement of lipoprotein cholesterol is a useful first step in the intervention against diseases such as atherosclerosis and ischemic stroke, and is important in determining what constitutes a vulnerable plaque in order to derive an effective means for stabilizing such plaque. Because cholesterol is carried in lipoprotein particles that differ in size and apolipoprotein composition, this variety of lipoproteins often make non-destructive differentiation of its composition difficult in the living vessel wall. As a result, most studies focus on in vitro methodologies for determination of plaque lipoprotein composition. However, production of artifacts is common using in vitro methods and has lead to confusion in the literature. At present, there is no in vivo assay for LDL and forms of oxidized LDL (oxLDL) in solid tissue atherosclerotic plaques. More specifically, there is currently no accurate non-destructive in vivo reference assay for LDL or apolipoproteins immobilized in the walls of living human arteries. Chemical analysis of lesions in vivo would provide for the kinetic characterization of atherogenesis which contribute to the understanding of lesion formation and growth. However, the near-IR spectrometry of plaque in vivo as described herein may thus facilitate assignment of patients to specific new drug interventions that may affect the course of atherosclerosis (such as TPA, which acts to block thrombi, Enlimomab, which acts to block granulocyte adhesion to the blood-vessel wall, Citicoline, which reduces free fatty acids, Lubeluzole, which interferes with the effects of nitric oxide, Tirilizad, which acts as a free-radical scavenger, or bFGF, which acts on growth factors) and/or surgical interventions such as bypass grafts or angioplasty and stents. The basic near-IR imaging techniques provided herein are based at least in part on the principle that many organic molecules absorb light in the near-IR spectrum in a specific manner. This creates unique reflectance spectra that can be analyzed to perform a non-destructive chemical analysis of tissue either through a microscope, or at a distance through a fiber-optic catheter. A Nd:YAG-pumped KTP/OPO laser system may be used with spectrometric catheters for use in analyzing atherosclerosis and markers of vulnerable plaque. The near-IR spectrometric catheter may be thus used for early detection of LDL uptake in the arterial wall even before the appearance of visible fatty streaks. Another object of the invention therefore is to provide near-IR laser spectrometric assays of plaque which may be performed with cardiac catheters in vivo to facilitate the assignment of patients to specific drug or surgical interventions that are selected to match their individual vulnerable plaque characteristics.

Other aspects of the invention are directed to the role of group V secretory phospholipase A2 (sPLA2), an important enzyme in inflammatory processes, in the generation of vulnerable atherosclerotic plaques. Near-IR imaging may be used to identify predetermined compounds such as sPLA2, and to survey for new compounds. For example, lysophosphatidylcholine (LPC) is a major product of sPLA2 action. Since there are no specific antibodies to LPC that could be used for immunohistochemical studies, its localization in various regions of plaque may be determined by near-IR imaging of histologic sections. Moreover, near-IR spectra may be obtained for lesions from animal studies overexpressing sPLA2 activity. These spectra, which may reflect a combination of elements potentially associated with vulnerability, can be compared with the spectra obtained in patients at sites proven to be vulnerable by occurrence of subsequent events. Spectra from the animal studies may thus identify a compound not yet suspected to be associated with vulnerability in humans. The role of serum amyloid A (SAA) has been also shown to be an important cofactor for sPLA2 activity, and associated with clinical events. Its role may be further elucidated by the invention, and will be measured in patients undergoing near-IR imaging. The overall importance of sPLA2 as a determinant of plaque vulnerability may be further recognized if sPLA2 is indeed determined to play a major role in this condition. An sPLA2 inhibitor may be thus used as first-line therapy for patients found to have a vulnerable plaque. In any event, the final decision on therapy in patients will be made on the basis of the best information available at the time of treatment. The invention provides an increased understanding as to the diagnosis, and treatment, of vulnerable coronary plaques. This information concerning sPLA2 may provide new therapeutic opportunities such as the development of a specific inhibitor of the isoform of the enzyme located in macrophages. The development of a low-risk method to identify vulnerable plaques in high-risk patients undergoing PTCA/stenting would greatly aid in the conduct of studies to diminish that risk with specific drug therapy. Individuals at increased risk of disruption of a vulnerable plaque may be assisted by the invention which creates the foundation for the development of interventions that prevent the sudden onset of a catastrophic coronary event.

It is another object of the invention to provide near-IR imaging of plaque composition and vulnerability in vivo. Near-IR spectroscopy may identify vulnerable lesions in the coronary arteries of living patients. In particular, vulnerable coronary plaque may be detected because of the unique advantages provided by the catheter-based near-IR imaging systems described herein despite the general difficulty in imaging coronary lesions. These catheter-based near-IR imaging systems provide possible prospective identification of vulnerable coronary artery plaques in living patients. Particular investigations may be conducted in accordance with the invention: to obtain additional calibration and blinded validation of near-IR imaging in ex vivo human autopsy specimens (blocks from aortas and coronary arteries); to test the ability of catheter-based near-IR imaging to detect vulnerable aortic plaque in vivo (in rabbits) with diet-induced atherosclerosis; to perform near-IR catheter-based mapping of coronary artery chemical composition in patients undergoing PTCA and/or stenting; and to identify rapid lesion progression by angiography and clinical events during subsequent years. When potentially high-risk patients are identified with near-IR signatures of plaques with lipid pools and thin caps, for example, they may be subject to a further therapy study to stabilize vulnerable plaques. Another object of the invention is to thus provide therapeutic methods and apparatus to stabilize plaques that have been characterized as vulnerable by using near-IR therapy to promote fibrosis or thickening of the thin fibrous caps covering these lipid pools to prevent their rupture or leakage. The subsequent treatments to be administered may further include an orally active matrix metalloproteinase inhibitor (MMPI), and, possibly, an inhibitor of Group v secretory phospholipase 2 (sPLA2). Patients may also be selected for intensive lipid lowering therapies if they were found to have vulnerable plaques.

In accordance with another aspect of the invention, it is further possible to determine the relationship between the prospective near-IR chemical map of the human coronary tree, and the rapid progression of coronary lesions as of one-year later which may be documented by angiographic and/or autopsy findings. These findings may be provided from a study involving a relatively large number of patients such as 600 or more undergoing angioplasty wherein three major coronary arteries are scanned for the presence of vulnerable plaques as described herein. There may be follow-up procedures for up to several years to determine the occurrence of subsequent cardiac events. The near-IR signature of sites or lesions that eventually progress to an event may be considered the near-IR sign or indicator of plaque vulnerability. This relationship may be used to construct a near-IR index of true vulnerability of coronary plaques in living patients. Various embodiments of the invention make this particularly feasible in that near-IR spectroscopy may identify plaques with a lipid pool and thin cap in vivo, and may be performed through a coronary catheter as described herein. A validated, prospective, near-IR index of vulnerability may be thus developed in accordance with the invention. Effective stabilization therapy may be identified thereafter, and may be widely used in the treatment of high-risk patients undergoing coronary interventions. Collagen degradation by MMPs and plaque inflammation have been demonstrated in atherosclerotic tissue, and well-tolerated, orally active inhibitors are also available. Studies of plaque stabilization in such patients may further yield information of great value for all individuals at risk of plaque disruption and coronary events. Additional objects and advantages of the invention will become apparent to those skilled in the art upon examination of the foregoing description of the invention which may be modified without departing from the scope of the invention.

BRIEF DESCRIPTION OF THE FIGURES

FIG. 1 provides an illustration of the near-IR spectrum for cholesterol.

FIG. 2 provides an illustration of the near-IR spectrum for lysophosphatidylcholine (LPC).

FIG. 11 provides a data table for the identification vulnerable plaque characteristics in humans by near-IR imaging.

DETAILED DESCRIPTION OF THE INVENTION

Figure 3:
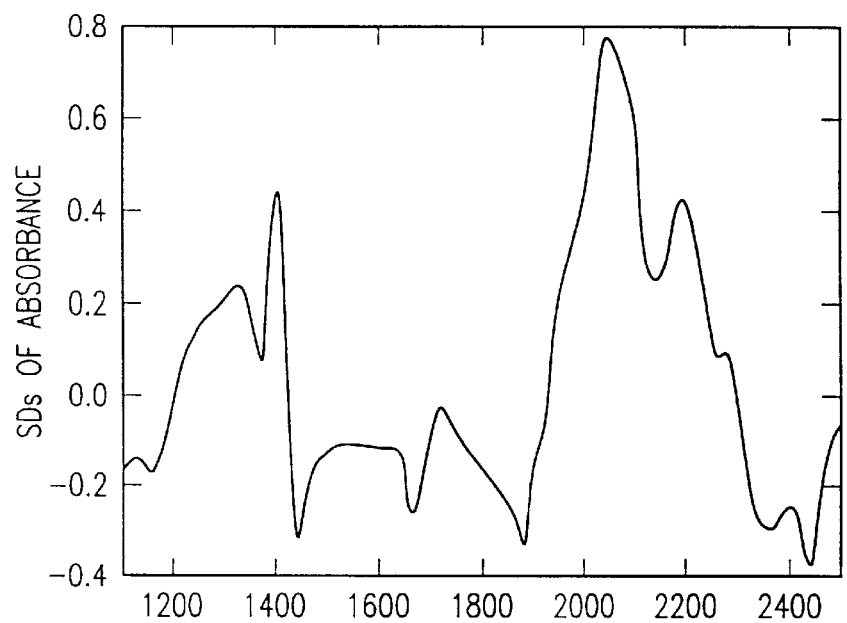
FIG. 3 provides an illustration of the near-IR spectrum for a fibrous cap associated with vulnerable plaques.

The present invention provides methods and apparatus for in vivo detection and characterization of vulnerable atherosclerotic plaques with near-infrared (IR) spectroscopy. Each of the disclosed embodiments may be considered individually or in combination with other variations and aspects of the invention. The near-IR spectrometric imaging techniques described herein may be used to non-destructively locate and identify low-density lipoprotein (LDL) cholesterol which may serve as an in vivo marker for the presence of vulnerable atherosclerotic plaques. Vulnerable plaques may be generally described as plaques that are prone, with or without a triggering activity or event of a patient, to events such as ulceration, rupture, erosion leading to thrombosis causing an acute syndrome. The characterization and risk assessment of clinical patients using near-IR laser spectrometric assays of vulnerable plaque in vivo may enable the assignment of patients to specific drug or surgical interventions selected to match individual plaque characteristics.

I. Applications for in vivo Identification and Characterization of Vulnerable Plaque The invention provides methods and apparatus for the identification and characterization of vulnerable plaques, particularly in coronary circulation, that may be readily implemented as part of an early detection and intervention program.

A. Prospective Identification of the Vulnerable Plaque

In general, a plaque that is formed with a large lipid pool, a thin fibrous cap and macrophage infiltration, is a plaque that may be considered vulnerable to disruption (Muller J E, Kaufmann P G, Luepker R V, Weisfeldt M L, Deedwania P C, Willerson J T, Mechanisms precipitating acute cardiac events: Review and recommendations of an NHLBI workshop, National Heart, Lung, and Blood Institute: Mechanisms Precipitating Acute Cardiac Events Participants, Circulation 1997; 96(9):3233–9 (cited references are incorporated herein by reference)). While lipid and macrophage-laden plaques are vulnerable to disruption, it is important to recognize the incomplete nature of the basis for supporting this hypothesis. Although large lipid pools and thin caps with macrophages have been identified in disrupted plaques, a prospective study has not been conducted to demonstrate that these features are predisposed to disrupt, even in an animal model. Also, such microanatomy does not account for the plaques that erode and produce thrombosis. However, the concepts of the present invention are directed to the identification and characterization of certain lesions (plaques with lipid pools and thin, weakened caps, or some other features) that are particularly vulnerable to disruption. These types of vulnerable plaques have been detected and identified prior to disruption, in part, by following the patients until a sufficient number of coronary events occurred (Uchida et al, Prediction of acute coronary syndromes by percutaneous coronary angioscopy in patients with stable angina, Amer Heart J 1995, 130 (2): 195–203). The events occurred with greater frequency at sites suspected to be vulnerable than at non-vulnerable sites. Given the present state of knowledge, and for purposes of avoiding confusion herein, the term vulnerable may describe the pathologic findings of a plaque having a large lipid pool, a thin cap, and an inflammatory infiltrate (Muller J E, Abela G S, Nesto R W, Tofler G H, Triggers, acute risk factors and vulnerable plaques: The lexicon of a new frontier, J Am Coll Cardiol 1994; 23:809–13). Vulnerable may also refer to plaques that may be identified in the future with near-IR imaging in accordance with the invention that also lead to a higher rate of events. A subset of plaques shown to be vulnerable by near-IR with supporting outcome data may be further characterized as vulnerable plaques as defined by histology. In any event, the identification of vulnerable plaques prior to disruption as described herein provides an enormous advantage in the prevention of cardiovascular disease, and further provides an opportunity to effect appropriate treatment which would convert such plaques to non-vulnerable plaques.

B. Near-IR Imaging For Identifying Vulnerable Coronary Plaques

The invention provides methods and apparatus to identify vulnerable coronary plaques in patients with near-IR spectrometry. These techniques are based on the absorbance of light in the near-IR spectrum, in a specific manner, by organic molecules. This creates unique reflectance spectra that can be used to obtain a chemical analysis of tissue in a non-destructive manner.

1. Features of Near-infrared Spectrometry.

The near-IR region of the electromagnetic spectrum, once regarded as having little potential for analytical work, has become one of the most promising for molecular spectrometry. The advent of inexpensive and powerful computers has further contributed to the surge of new near-IR spectrometric applications. The near-IR region is usually estimated to include wavelengths between 700 nm (near the red end of the visible spectrum) and 3000 nm (near the beginning of infrared stretches of organic compounds). Absorbance peaks in the near-IR region originate from overtones, from combinations of the fundamental (mid-IR) bands and from electronic transitions in the heaviest atoms. For example, C—H, N—H, and O—H bonds are responsible for most major absorbance peaks observed in the near-IR spectrum, and near-IR spectrometry is used chiefly for identifying or quantifying molecules that contain unique hydrogen atoms. Near-IR spectrometry is therefore used routinely for quantitative analyses of water, alcohols, amines, and any compounds comprising C—H, N—H, and/or O—H groups. It has been also used industrially for a number of years to determine the sites and amount of saturation in unsaturated fatty acid esters (Wetzel D, Near-infrared reflectance analysis: Sleeper among spectroscopic techniques, Anal Chem 1983; 1165A–76A). In addition, near-IR spectrometry is characterized by low molar absorptivities and light scattering which permit conservation of time and materials in comparison to more conventional analytical methods because of various reasons including: 1) analysis times under one second are possible; 2) simultaneous multi-component analysis is the norm; 3) no sample preparation is usually required for liquids, solids, or gases; 4) non-invasive and non-destructive analysis is possible; 5) the cost-per-analysis is very low (no reagents are used); 6) physical properties and biological effects can be calculated from spectra of samples; 7) automated correction of background and interferences is performed in instruments using computer algorithms; 8) detection limits can be very low; 9) samples sizes ranging "from picograms to planets" can be analyzed; and 10) molecular structural information can be derived from spectra.

2. Technical Aspects of Near-IR Imaging

Near-IR spectrometry typically uses a tunable light source (filter wheel, monochromator, interferometer or laser) external to the experimental subject to determine the chemical composition of a sample. Detectors can be single elements for spectrometry, or may be detector arrays in cameras for spectrometric imaging. Modem near-IR spectrometers and sampling techniques have improved to the point that it is possible to analyze intact finished pharmaceutical products, and even analytes in living human patients. In vivo near-IR spectrometry had been plagued historically by problems with high water absorbance in tissue, light scattering, peak overlap, and peak shifting with temperature and sample-matrix composition. However, more intense and more stable light sources, more efficient detectors (and in many cases, more efficient imaging detectors), and improved methods of obtaining rapid wavelength selectivity have permitted application of near-IR imaging to increasingly complex biological and medical problems. The importance of these instrumental advances is evident in the application of near-IR spectrometry to atherosclerosis and stroke research. Using a specially modified IR video camera, different band pass filters or tunable lasers permit collection of image spectra over the range of 1000–4000 nm (near-IR and IR spectral range) (Dempsey R J, Davis D G, Buice R G, Lodder R A, Biological and medical applications of near-infrared spectrometry, Appl Spectrosc 1996; 18A–34A).

3. Methods of Utilizing Near-IR Imaging a) Identification of specific compounds

A major advantage of using near-IR spectrometric imaging over ultrasonic and magnetic resonance imaging (MRI) is its ability to perform simultaneous, multi-component chemical analyses with a single near-IR spectral scan. The near-IR spectrum of a sample, which is generated from combinations and harmonics of fundamental molecular motions, contains more chemically specific information than is ordinarily available in an ultrasonic absorbance spectrum. At the same time, the large number of near-IR chromophores, and the intrinsically high signal-to-noise ratio (S/N) of near-IR instruments, give near-IR spectrometry improved sensitivity to lipids and collagens in samples such as vulnerable coronary artery plaques, as described herein, than is available through MRI. Near-infrared spectrometry has been used to identify thousands of chemicals, including such biologically interesting analytes as cholesterol, HDL, and LDL (Cassis L A, Lodder R A, Near-IR imaging of atheromas in living arterial tissue, Analytical Chem. 1993; 65(9):1247–56), glucose and albumin (Drennen J K, Gebhart B D, Kraemer E G, Lodder R A, Near-infrared spectrometric determination of hydrogen ion, glucose, and human serum albumin in a simulated biological matrix, Spectroscopy 1990; 28–36).

b) Identification of Spectral Difference Between Different Types of Complex Tissues Near-infrared spectrometry has been used for measurement of cerebral oxyhemoglobin and deoxyhemoglobin in adults (Elwell C E, Matcher S J, Tyszczuk L, Meek J H, Delpy D T, Measurement of cerebral venous saturation in adults using near infrared spectroscopy, Adv Exp Med Biol 1997; 411:453–60). Non-invasive near-IR spectrophotometry of gerbil brain tissue in vivo has been shown to discriminate between adult (three to four months of age) and aged (18 to 20 months of age) brains, as well as between brains exposed to five and ten minutes of ischemia (Carney J M, Landrum W, Mayes L, Zou Y, Lodder R A, Near-IR spectrophotometric monitoring of stroke-related changes in the protein and lipid composition of whole gerbil brains, Anal Chem 1993; 1305–13). It has been also used transarterially in the carotid arteries of human patients to identify fibrous caps, lipids, thrombus, ulceration and necrosis with an indium antimonide focal plane array video camera. Inverse principal axis transformation revealed the linear combination of lipoproteins that correlated to necrosis in the plaque pathology reports (nc=29 patient plaques for calibration, nv=29 patient plaques for cross validation). The data were normalized by z-scoring, so a flat line at y-axis=0 represented the average gel appearance. Positive deviations from y=0 represented more protein in the molecular mass region than the average gel, while negative deviations represent less protein in the molecular mass region than the average gel. A major difference between the necrotic plaques and the plaques without necrosis is the presence of a 128 KD lipoprotein in the necrotic plaques.

4. Potential Advantages of Near-IR for Identifying Vulnerable Coronary Plaques

The methods and apparatus provided herein for identifying and characterizing vulnerable coronary plaques demonstrate effective chemical sensitivity and specificity. As described above, a major advantage of near-IR spectrometric imaging over ultrasonic and MRI is its ability to perform simultaneous multi-component chemical analyses using a single near-IR spectral scan. Moreover, near-IR spectrometry can be implemented in a catheter as described herein which are even smaller than those devices used in ICUS, and permit high resolution (both spatial and chemical) analyses to be performed within arterial vessels of living patients. The cost of catheters described herein may be relatively low enough to make them disposable, single-use devices. The high intensity and tunability of external cavity tunable diode lasers also makes intravascular near-IR imaging a durable and relatively inexpensive solution. The rapidity of high S/N spectral data collection further enables complete chemical maps of blood vessels like coronary arteries to be readily obtained during an interventional PTCA. The invention thus provides an accurate non-destructive in vivo reference assay for most lipids and proteins immobilized in the walls of living human arteries. In addition to detecting vulnerable plaque, chemical analysis of lesions in vivo may be accomplished which may further the kinetic study of atherogenesis and contribute to the understanding of lesion formation and growth. The methods and apparatus described herein may play key roles in the monitoring the progression or regression of, the vulnerability of lesions. Near-IR spectrometry of plaque in vivo may facilitate assignment of patients and plaques to specific new drug interventions that affect the course of atherosclerosis. Better treatment programs may be thus designed that focus on these mechanisms.

C. Clinical Issues

1. Prognosis of Post-PTCA/Stenting

The near-IR imaging described herein may be performed on patients undergoing PTCA/stenting who will already have a wire inserted in a culprit artery for clinical reasons. A rationale for near-IR imaging in these patients may be that during the following year following PTCA/stenting, approximately 10% will experience death, myocardial infarction (MI), or require repeat revascularization because of rapid progression of a plaque other than the one originally treated. It is the progression of such plaques that has substantially led to the inability of PTCA/stenting and CABG to prevent subsequent MI in randomized studies.

2. Therapy to Stabilize Vulnerable Plaques

Different therapies have been developed thus far for stabilizing vulnerable plaques. These and future treatments may be carried out in light of the benefits conferred by the invention as described herein.

a) Lipid Lowering

In contrast to the experience with revascularization, intense lipid lowering with statins has been found to prevent MI. The observation that the degree of prevention of MI exceeded the modest improvements in fixed stenoses, has led to some speculation that the therapy stabilized vulnerable plaques. While this may occur, even when lipid lowering therapy is administered maximally, the event rate for this group remains high, and additional therapies are still generally needed.

b) Matrix Metalloproteinases

Matrix metalloproteinases (MMPs) are a group of proteolytic enzymes that can digest collagen and elastin in the extracellular matrix. Several studies have identified MMPs in animal and human vulnerable plaques. The MMPs within plaques are believed to be secreted by activated macrophages (Matrisian L M, The matrix degrading metalloproteinases, Bioessays 1992; 14:455–63) and to be at least in part responsible for extracellular matrix degradation leading to weakening of plaques fibrous cap, and plaque rupture with its clinical sequelae (Henney A M, Wakeley P R, Davies M J et al, Localization of stromelysin gene expression in atherosclerotic plaques by in situ hybridization, Proc Natl Acad Sci USA 1991; 88:8154–8). Thickness and collagen content of the fibrous cap are important for the stability of the plaque (Loree H M, Kamm R D, Stringfellow R G, Lee R T, Effects of fibrous cap thickness on peak circumferential stress in model atherosclerotic vessels. Circ Res 1992, 71, 850–858). The plaque disruption occurs most frequently at sites where the fibrous cap is the thinnest and the most heavily infiltrated by foam cells (Friedman M, The coronary thrombus: Its origin and fate, Hum Pathol 1971; 2:81–128). The release of proteolytic enzymes, in particular MMPs, by these cells has been suggested as a mechanism leading to plaque vulnerability and rupture (Richardson P D, Davies M J, Born G V, Influence of plaque configuration and stress distribution in fissuring of coronary atherosclerotic plaques, Lancet 1989; 2:941–4; Davies M J, Richardson P D, Woolf N, Katz D R, Mann J, Risk of thrombosis in human atherosclerotic plaques: Role of extracellular lipid, macrophage and smooth muscle content, Br Heart J 1993; 69:377–81; Seppo T, Kevin D, Marina F et al, Interstitial collagenase expression in human carotid atherosclerosis, Circulation 1995; 92:1393–8; Zorina G, Galina S, Roger K, Stephen C, Libby P, Macrophage foam cells from experimental atheroma constitutively produce matrix-degrading proteinases, Proc Natl Acad Sci USA 1995; 92:402–6). MMPs have also been found to be active in spread of tumors (Stetler-Stevenson W G, Liotta L A, Kleiner D E, Extracellular matrix 6: Role of matrix metalloproteinases in tumor invasion and metastasis, FASEB J 1993; 7:1434–41; Brown P, Giavazzi R, Matrix Metalloproteinase inhibition: A review of antitumour activity, Annal of Onc 1995; 6:967–74) and other conditions such as rheumatoid arthritis (Yoshihara Y, Obata K, Fujimoto N, Yamashita K, Hayakawa T, Shimmei M, Increased levels of stromelysin-1 and tissue inhibitor of metalloproteinases-1 in sera from patients with rheumatoid arthritis, Arthritis Rheum 1995; 38:969–75), osteoarthritis (Manicourt D H, Fujimoto N, Obata K, Thonar E J, Serum levels of collagenase, stromelysin-1, and TIMP-1, Age and sex related differences in normal subjects and relationship to the extent of Joint involvement and serum levels of antigenic keratin sulfate in patients with osteoarthritis, Arthritis Rheum 1994; 37:1774-83), liver cirrhosis (Takahara T, Furui K, Funaki J et al, Increased expression of matrix metalloproteinase-II in experimental liver fibrosis in rats, Hepatology 1995; 21:787–95), Crohn's disease and emphysema (Shapiro S D, Elastolytic metalloproteinases produced by human mononuclear phagocytes, Potential roles in destructive lung disease, Am J Respir Crit Care Med 1994; 150:S160–S164).

Activity of MMPs in tissue is regulated at many levels. Initially, their expression is modulated at the gene level, and moreover, they are secreted in proenzyme form and require activation. Further modulation is primarily achieved by a balance between enzyme concentration/activity and nonspecific (2-macroglobulin) and specific (tissue inhibitors of metalloproteinases -TIMPS) inhibitors. In addition to naturally occurring inhibitors, a number of designed inhibitors have been developed, and are in different phases of testing for their investigational and clinical utility. Most of the human studies to date are at the stage of phase I/II clinical trials. The safety profile of synthetic MMPs inhibitors in therapy of prostate, lung, colon and breast malignancies is satisfactory. Agouron Pharmaceuticals Inc., for example, has designed and produced several MMP inhibitors (MMPI). One inhibitor has thus far demonstrated relatively powerful activity against stromelysin, and has been quite well tolerated in over 150 patients with prostate cancer. At the present time, there are no known published studies relating to the use of natural or synthetic MMPIs to inhibit plaque disruption and/or accelerate transition to mature, stable, dormant plaque. However, in experimental ex vivo models involving human atherosclerotic plaques and activated macrophages, MMP inhibitors have been shown to substantially decrease extracellular matrix degradation. In summary, MMPs may be indeed involved in plaque vulnerability, and well-tolerated inhibitors are presently available for human studies which may be used in accordance with the principles of the invention.

c) sPLA2 inhibitors

While the role of sPLA2 in vulnerability has not received as much attention as MMPs, this enzyme and the products it creates, may play a role in weakening plaque, perhaps at a more basic level. Further research may clarify its role, and if it is active, inhibitors for clinical use may be also obtained and used in combination with other aspects of the invention.

D. Early Detection and Characterization of Vulnerable Plaque

Although the procedures and apparatus provided herein may detect vulnerable coronary plaques to help identify groups at higher risk, most individuals actually experience their first MI and/or a coronary death prior to their first catheterization. Significant benefits may be still achieved nonetheless if the invention were directed to a sample subset of 400,000 patients who undergo PTCA/stenting. The treatment for this group of the population may lead to less invasive means of detection and treatment that are applicable to the much larger group of individuals with known coronary artery disease (CAD), or are at high risk for CAD. In accordance with the principles of the present invention, near-IR mapping may be performed with these patients who may undergo diagnostic catheterization for purposes of comparison to established a near-IR vulnerability index. The procedure may be highly predictive of subsequent events, and may offer safe and efficacious treatment for identified plaque vulnerability in subsequent cases.

II. Preliminary Studies and Discussion

The following section is a description of near-IR imaging studies in laboratory settings that included various applications for the methods and apparatus provided in accordance with the principles of the invention.

A. Near-IR Spectrometry

1. Near-IR Analytes Measured In vitro

The invention incorporates technology relating to near-IR of analytes measured in vitro including quantitative and qualitative near-IR spectrometry of cholesterol, cholesterol esters, cholesterol monohydrate, and lipoprotein cholesterol in blood serum and in plaques (Cassis L A, Yates J, Symons W C, Lodder R A, Cardiovascular near-infrared imaging, J Near-Infrared Spectrosc 1998; Lodder R A, Moorehead W, Robertson S P, Rand PHGM, Assessment of the Feasibility for Determination of Cholesterol and Other Blood Constituents by Near-Infrared Reflectance Analysis, Talanta 1989; 36:193–8). The spectrum of cholesterol has unique identifying features in a so-called water window where water has minimal absorbance (i.e., no vibrational energy absorbance peaks) between about 1450 and 1950 nm as shown in FIG. 1. These absorbance-wavelength features may be used to identify and quantify cholesterol simultaneously with other components in mixtures. Because light scattering decreases with the fourth power of wavelength, and because this spectral region is far removed from the hemoglobin electronic absorbance that lies below 1000 nm, light penetration through whole blood is typically very good. As shown in FIG. 2, lysophosphatidylcholine (LPC) also has a unique near-IR spectrum that can be used to detect the activity of sPLA2 in inflammatory processes. The near-infrared diffuse reflectance spectrum of collagens may be used to detect the presence of fibrous caps on vulnerable plaques, and to determine the size of the cap with near-infrared imaging as shown in FIG. 3.

2. Near-IR Imaging through Whole Blood

Figure 4:
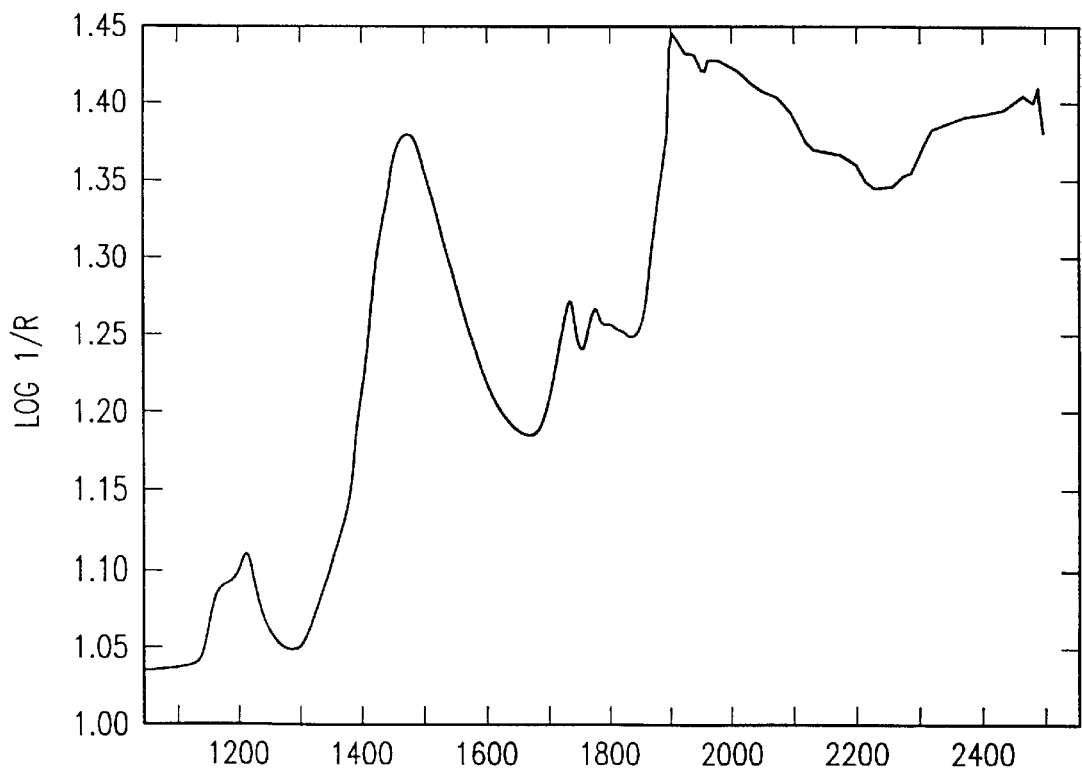
FIG. 4 illustrates the spectrum for rat aortas through whole blood and saline.

Near-IR light in the 1600–1900 nm wavelength region penetrates sufficiently through whole blood to enable spectroscopy within blood vessel walls as shown in FIG. 4 (Cassis L A, Lodder R A, Near-IR imaging of atheromas in living arterial tissue, Analytical Chem. 1993; 65(9):1247–56). Fiber-optic probes and a monochromator system with a 1000 W tungsten-halogen lamp was used to obtain spectra of the aortas of rats. The natural reduction in scattering of light in this long wavelength region and the reduced absorbance of water in this water window, combined to permit the collection of good-quality spectra In general, the fiber-optic probe may be operated relatively close to the vessel wall (<1 mm) to minimize interference from whole blood. Spectra of the aorta may be obtained through both whole blood and phosphate-buffered saline (PBS) as demonstrated in FIG. 4, and are shown with solid and dashed lines. The spectra are virtually identical and overlap over most of the wavelength range examined.

Figure 5:
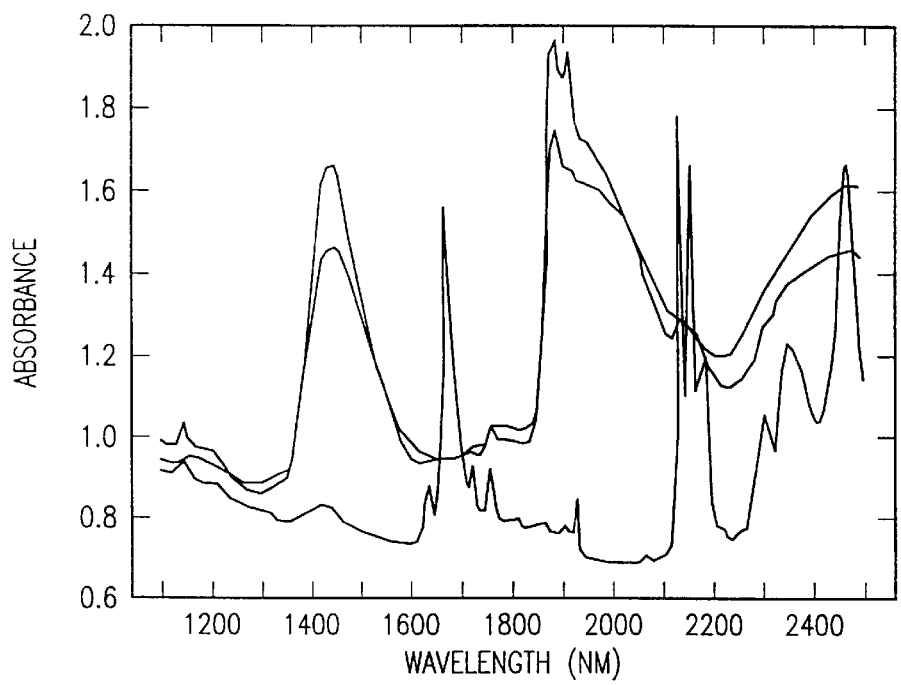
FIG. 5 illustrates the spectrum for polystyrene through a rat aorta.

In a further test of the penetration ability of near-IR light, the spectrum of a polystyrene wavelength-calibration standard may be obtained through a rat aorta as shown in FIG. 5 (Cassis L A, Lodder R A, Near-IR imaging of atheromas in living arterial tissue, Analytical Chem. 1993; 65(9):1247–56). The spectrum of the polystyrene may be obtained trans-arterially by transmitting the light from a fiber-optic probe placed on the outside of the aorta, through both walls of the aorta, then through the polystyrene, reflected back off a mirror, and back through the polystyrene and both walls of the aorta to the detector. The total path length was 4 mm, which is generally deeper than a human coronary plaque. FIG. 5, depicts three spectra: the lowest (the spectrum of the polystyrene standard alone), the middle (somewhat featureless spectrum is the spectrum of the aorta), and the upper spectrum (the spectrum of the polystyrene obtained through the aorta). The spectral absorbance peaks of polystyrene show through well in the 1100–1300 nm and 1600–1850 nm wavelength regions. The largest peaks of polystyrene (the triplet at 2140–2200 nm) may even show through somewhat. although they may be greatly diminished by the large background absorbance of water.

3. Imaging the Rabbit Aorta Through a Catheter

Figure 6:
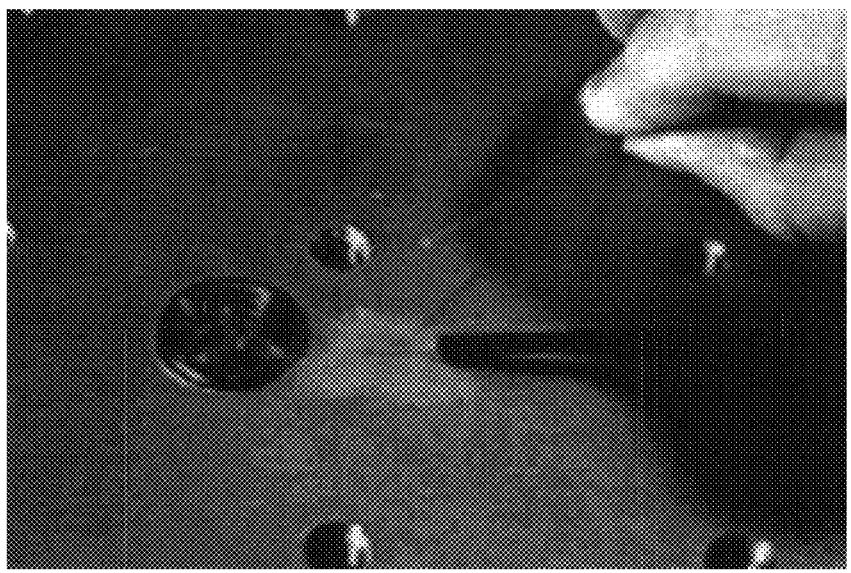
FIG. 6 is an illustration of a near-IR catheter used in vivo shown while illuminated with a HeNe laser where light can be seen returning down a receiving optical fiber from the catheter tip when the catheter is held against an optical table.

Some of the studies described herein were conducted using the atherosclerotic rabbit model introduced by Constantinides et al. (Constantinides P, Chakravarti R N, Rabbit arterial thrombosis production by systemic procedures, Arch Pathol 1961; 72:197–208). This rabbit model develops vulnerable plaques prone to rupture with subsequent thrombosis (Abela G S, Picon P D, Friedl S E et al, Triggering of plaque disruption and arterial thrombosis in an atherosclerotic rabbit model, Circ 1995; 91:776–84). The plaque generation feature of the model (not the triggering aspect) was used to test the near-IR catheters provided herein. In the imaging of rabbit aortas, a Nd:YAG-pumped KTP/OPO laser system was used to test experimental spectrometric catheters developed for use in several projects investigating atherosclerosis and markers of vulnerable plaque. The purpose of this experiment was to test the hypothesis that a near-IR spectrometric catheter is capable of early detection of cholesterol uptake in the arterial wall through whole blood even before the appearance of visible fatty streaks. The light source used in the catheter experiments was a laser system consisting of a MIRAGE 3000B Mid-Infrared Optical Parametric Generator and a Continuum NY81–10 Nd:YAG Pump Laser. The system provides tunable near-IR light with a wavelength from 1.4 to 4.1 micrometers and an effective power of 3.3 million watts. The spectra were scanned in the water window between 1650 and 1780 nm, where LDL cholesterol is generally known to have two major peaks. The catheters were constructed in-house from communications-grade optical fibers as illustrated in FIG. 6. The distal reflector tip of the catheter was constructed of gold-plated steel and was 450 micrometers in diameter (Sicon, Berlin, Germany). The diameter of the reflector was selected to match that of the combined transmitting and receiving fiber-optic bundles. One bundle of seven optical fibers was used to transmit light onto the blood vessel wall, while the remaining fibers were used to collect light scattered by the wall and return it to a PbS detector for analysis. The dimensions of the completed catheter assembly were designed to provide a close fit within the artery. The close fit reduced catheter motion with respect to the vessel wall and reduced the optical path length traversed through whole blood. Spectral data were smoothed using cubic splines, treated with multiplicative scatter correction to reduce baseline variations, and analyzed using the BEST (Bootstrap Error-Adjusted Single-Sample Technique) algorithm (Cassis L A, Lodder R A, Near-IR imaging of atheromas in living arterial tissue, Analytical Chem. 1993; 65(9):1247–56) implemented in Speakeasy (Speakeasy Computing Corp., Chicago, Ill., USA). Video clips were prepared in Quicktime format (Apple Computer Corp., Cupertino, Calif., USA) or AVI format using Media Studio (Ulead, Torrance, Calif, USA).

Figure 7:
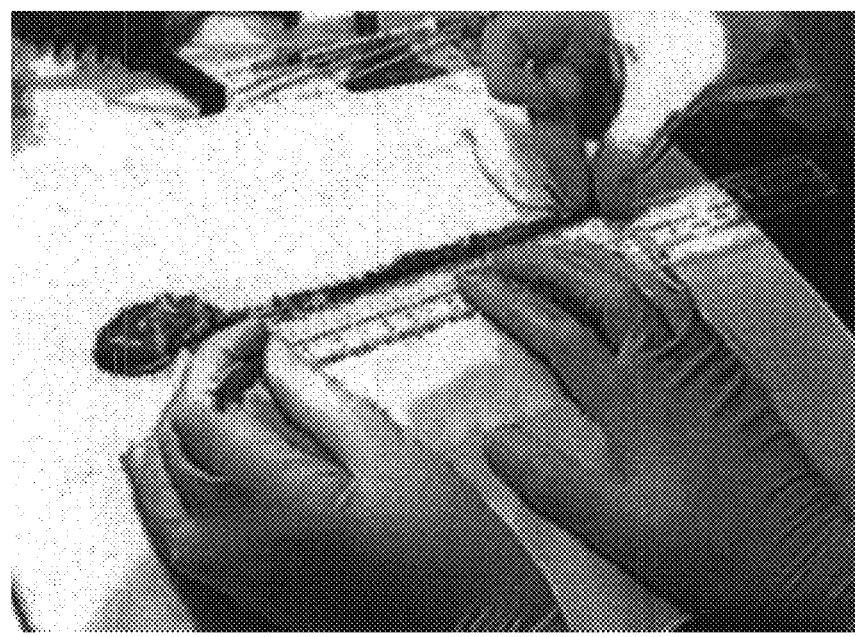
FIG. 7 illustrates a catheter laid beside the heart and aorta of a rabbit, and a meter stick wherein a suture is tied on the catheter at the point of maximum insertion to enable the penetration to the aortic arch to be determined by measuring the distance between the suture and the femoral artery at each location where spectra may be obtained.

In this study, rabbits were maintained on a high-cholesterol (2%) diet for 6 weeks to create fatty streaks in their arteries. The rabbits were maintained for 6 weeks on high-cholesterol chow. The rabbits were anesthetized with atropine sulfate as a preanesthetic (0.1 mg/kg, i.m.) followed by ketacet (35 mg/kg, i.v.) and xylazine (5 mg/kg, i.v.). With the rabbit anesthetized, an incision near the femoral artery provided access to the aorta. The catheter included a small near-IR fiber-optic probe that was connected to the tunable laser and a detector, A/D, and computer. The laser was necessary to provide enough light to obtain usable spectra through the intervening whole blood and the arterial tissue. The catheters were inserted into the femoral artery and advanced to the aortic arch. As shown in FIG. 7, a suture was tied on the catheter at the point of maximum insertion to enable the penetration to the aortic arch to be determined by measuring the distance between the suture and the femoral artery at each location where spectra were obtained. The catheter was withdrawn in 1 cm increments, and spectra of the vessel wall were obtained at each increment. As the catheters were slowly withdrawn, near-IR spectra of the aorta were collected. Following the in vivo scanning with the tunable-IR laser, the animals were euthanized by an overdose of anesthetic, and the heart and aorta were removed. As with most traditional techniques, vascular tissue is removed from an animal before cholesterol and ox-LDL can be assayed. One advantage provided by near-IR imaging provided herein is that repeated analyses are possible for the same lesion in the same animal during lesion formation and/or treatment. These techniques enable the development of: tests for plaque vulnerability, tests of theories as to lesion formation, and tests of lesion rupture or erosion that are not typically possible with traditional analytical techniques.

Figure 8:
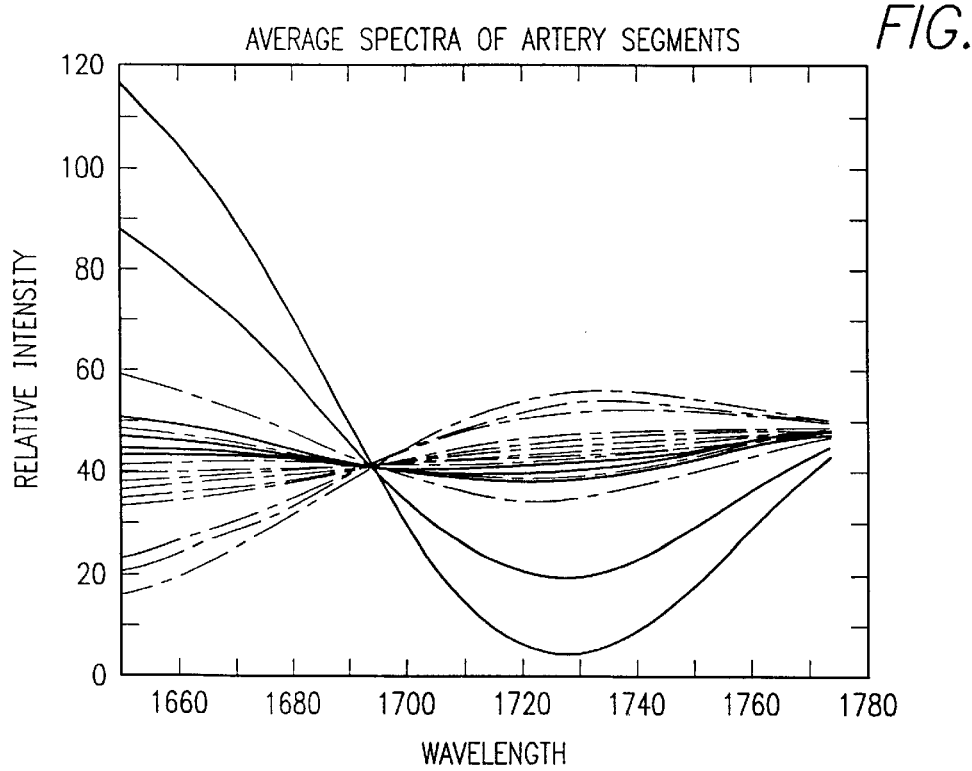
FIG. 8 shows the average near-IR spectra from a 1-cm aorta segment of a control and a cholesterol-fed rabbit wherein the solid lines represent spectra of the control aorta, and the dot-dashed lines represent the spectra of the cholesterol-treated aorta.

Furthermore, the aorta was measured, examined, and all physical aspects recorded. The excised heart and aorta were photographed and scanned with a conventional spectrometer as a control for the laser procedure. The aorta was cut into 1 cm sections and retained for extraction of lipoproteins in the lesion and analysis of the extract by density-gradient ultracentrifugation and SDS-PAGE (Dempsey R J, Cassis L A, Davis D G, Lodder R A, Near-infrared Imaging and Spectroscopy in Stroke Research: Lipoprotein Distribution and Disease, Ann. N.Y. Acad. Sci. 1997; 820:149–69). The average spectra from each artery segment of a control rabbit and a cholesterol-fed rabbit are depicted in FIG. 8. The spectra were obtained over a wavelength range where LDL and oxLDL cholesterol have absorbance signals (Cassis L A, Lodder R A, Near-IR imaging of atheromas in living arterial tissue, Analytical Chem. 1993; 65(9):1247–56). The solid lines represent spectra of the control aorta, while the dot-dashed lines represent spectra of the cholesterol-treated aorta. The cholesterol-fed animals showed a larger signal in the 1700–1800 nm lipid region of the spectra. There was some observed overlap between the spectra obtained from the cholesterol and control aortas. Several reasons for the overlap may include: (1) some LDL uptake by the control vessel wall is normal, as LDL cholesterol is needed to synthesize cell membranes for natural growth in the young animal; (2) atherosclerosis is a diffuse disease, and some diseased area of the vessel with LDL uptake will inevitably be near an area of normal vessel wall with relatively little LDL uptake; and (3) the uptake of LDL for 6 weeks is not enough to cause visible fatty streaks to appear, which usually requires 12 or more weeks. Nevertheless, the spectra appear to be different in the lipid region upon simple inspection. Statistical analysis of the spectra also reveals differences. The spectral data were analyzed with the BEST algorithm. The calibration set comprised spectra of normal arterial endothelium. The distance in multidimensional BEST SDs of each spectrum of each pixel on the vessel wall was measured to the center of the calibration set of normal (control) arterial endothelium. The distances ranged from 0.57 to 2.35 SDs for the control rabbits, and from 0.45 to 4.88 SDs for the cholesterol-fed rabbits. In summary, near-IR spectroscopy successfully identified cholesterol fed aortas from the control group.

Figure 9:
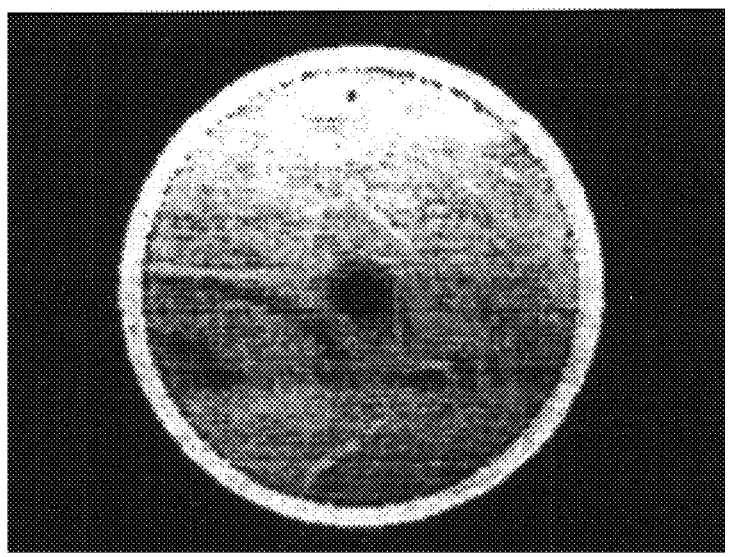
FIG. 9 provides a representative frame from a control video clip where increased LDL uptake is represented as a darker gray color.
Figure 10:
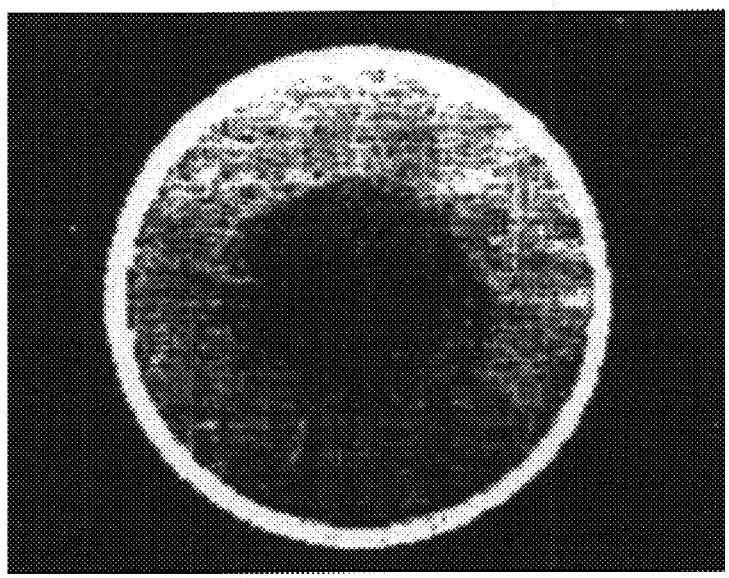
FIG. 10 provides a representative frame from a cholesterol-fed video clip where increased LDL uptake is represented as a darker gray color.

Quicktime videos were constructed from the image data obtained as the catheters were moved through the arteries. A representative frame from the control video clip is provided in FIG. 9, while a representative frame from the cholesterol-fed video clip is shown in FIG. 10. In the video clips, increasing uptake of LDL were represented as increasing red color (gray areas=little LDL, red areas=increased LDL). In FIG. 9 and FIG. 10, increased LDL uptake is represented as a darker gray color. The uptake of LDL is a natural process in young rabbits, making some pink areas visible even in the control vessel. Although six weeks on high-cholesterol chow is generally not long enough for the subject to develop actual lesions, analysis of the near-IR results did show significantly increased LDL uptake by the experimental subject as compared to the control, even at this early stage. No oxidation of the LDL cholesterol was noted in the vessel wall of either the cholesterol-fed or control rabbits. This result is not surprising considering the young age of the rabbits and the short duration of the study. In conclusion, early lesions were detected in vivo using near-IR spectrometric imaging with an intravascular fiber-optic catheter before the lesions were visible on gross examination. The observation of these pre-vulnerable plaques, when combined with similar measurements on grossly visible lesions made in humans, suggest that near-IR spectrometry is useful in detection of vulnerable plaques at nearly all stages of development. The non-destructive chemical and structural analysis of single lesions over time permits the discovery of markers for vulnerable atherosclerotic plaque. Finding such markers is an important problem because it may be determined that plaque vulnerability is a complex function of fibrous cap thickness, lipid pool size, stresses on plaque parts, and composition of the fibrous cap and lipid pool (which influences factors like thrombogenicity). Near-IR imaging spectrometry may be ideally suited to measure these plaque vulnerability parameters in accordance with the principles of the invention.

4. Blinded Identification with Near-IR Imaging of Vulnerable Plaques in Human Aorta Autopsy Specimens Near-IR spectrometry was further utilized through a fiber-optic bundle in accordance with the principles of the invention to identify vulnerable plaques in human tissue. A human aorta was scanned post-mortem. The aorta was opened and pinned down on a linear translation stage to enable the positions of the scans to be recorded. Thirty-one spectra were collected along 1 cm wide linear tracks oriented coronally, every 1.5 mm, using a 3 mm wide collection aperture. The tracks were marked for histological comparisons by attaching latex strips parallel to the tracks using a cyanoacrylate ester glue. The spectral scans covered the wavelength range from 1100 to 2200 run in 10 nm increments. The thirty-one tissue sections were examined by histology to identify thin fibrous caps and/or large lipid pools. Fifteen of the reference analyses were used to calibrate the near-IR method. In a blinded examination of the remaining sixteen sections, near-IR spectrometry correctly identified all specimens, thereby demonstrating 100% sensitivity and specificity for detection of large lipid pool and thin fibrous cap as summarized in FIG. 11.

5. Imaging through The Baxter Angioscopic Catheter

Figure 12:
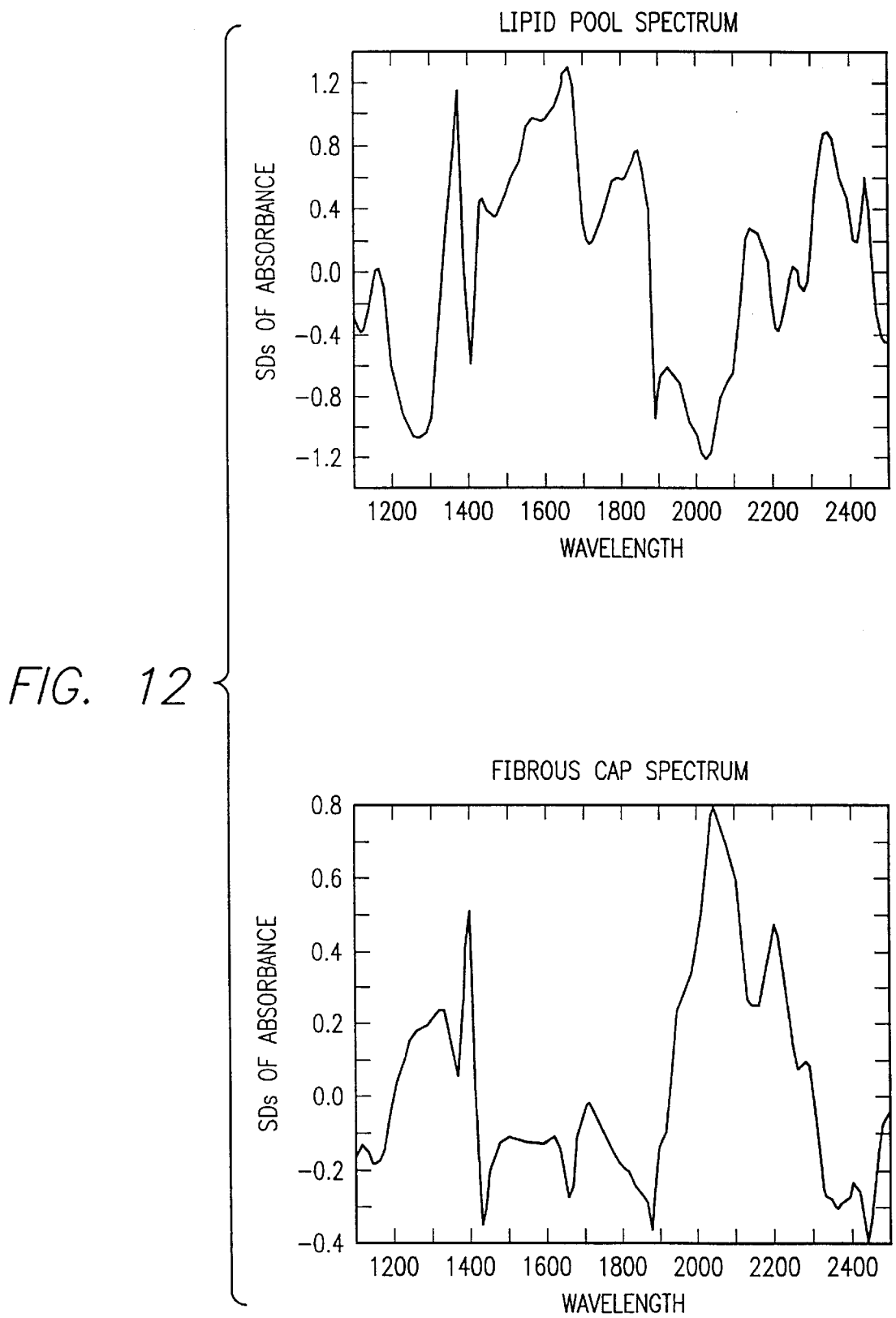
FIG. 12 illustrates the spectra of a lipid pool and fibrous cap associated with human vulnerable plaque.

Ex vivo imaging was performed through a Baxter angioscopic catheter designed for use in human arteries. The catheter includes a channel for a guide wire, two fiber-optic bundles to carry tunable laser light to the artery, and one indexed fiber-optic bundle to carry an image back to a camera through a video relay lens. A 1.5 mm O.D. version of the catheter was obtained for testing, as it represents the largest version of the catheter that could probably be used in the human coronary artery without occlusion of the vessel. A visible-light image of a lipid-filled plaque section obtained from a human aorta appears in FIG. 12. This plaque contains a fibrous cap and a few cholesterol crystals. FIG. 12 further provides a false-color near-infrared image of the same plaque appears. Both images were obtained using the Baxter indexed fiber-optic angioscope but with different digital cameras. In the false-color image, violet represents the lowest absorbance while red represents the highest absorbance. The software used in the spectrometric imaging system enables users to locate a feature of interest, click on it with a mouse, and obtain the full near-infrared spectrum of the target from the InSb focal plane array in the digital near-IR camera. Normalized near-infrared spectra of fibrous cap and lipid pool are also shown in FIG. 12. Normalization of near-infrared spectra, by subtraction of the mean absorbance at each wavelength from the absorbance at each wavelength at each pixel, and dividing that amount by the standard deviation of the absorbances at each wavelength, is a common practice in analysis of near-IR spectra to eliminate baseline variations and to reduce the effects of variation in water content on the spectra. Without normalization and spectral reconstruction by inverse principal axis transformation, the high molar absorptivity of water would most likely cause small variations in the amount of water to mask larger variations in the content of more interesting analytes.

The Baxter catheter demonstrated good spatial resolution in the forward direction. The company also provides reflector tips that enable the angioscope to look to the side at an angle of 45 degrees. The angioscope may be fitted with a 90 degree reflector tip like that used in the rabbit studies to minimize the optical path length through whole blood, and to maximize the scattered light signal from the plaques in the arterial wall.

B. Prospective Identification and Characterization of Vulnerable Plaques

Figure 13:
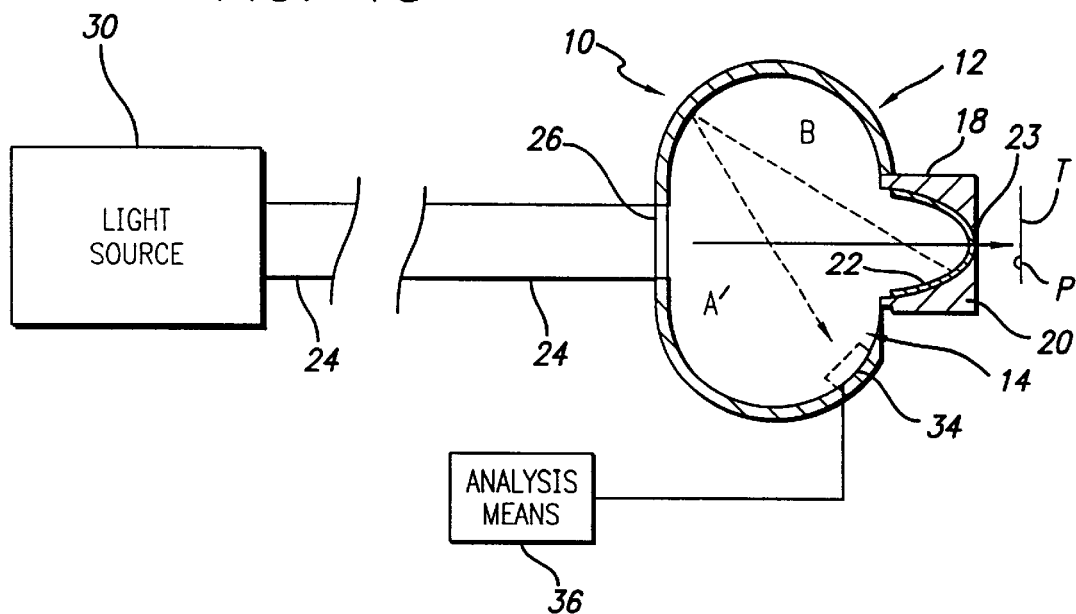
FIG. 13 is a simplified representation of one embodiment of the apparatus provided by the invention that includes a compound parabolic concentrator for the analysis of tissue.
Figure 14:
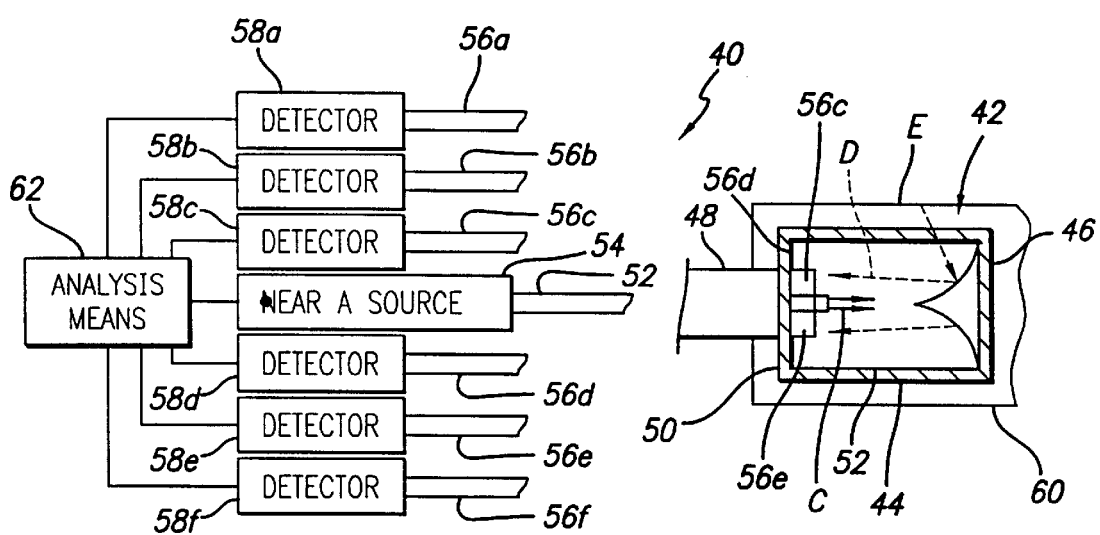
FIG. 14 is a simplified representation of another embodiment of the invention that includes an inverted, substantially cone-shaped reflector.
Figure 15:
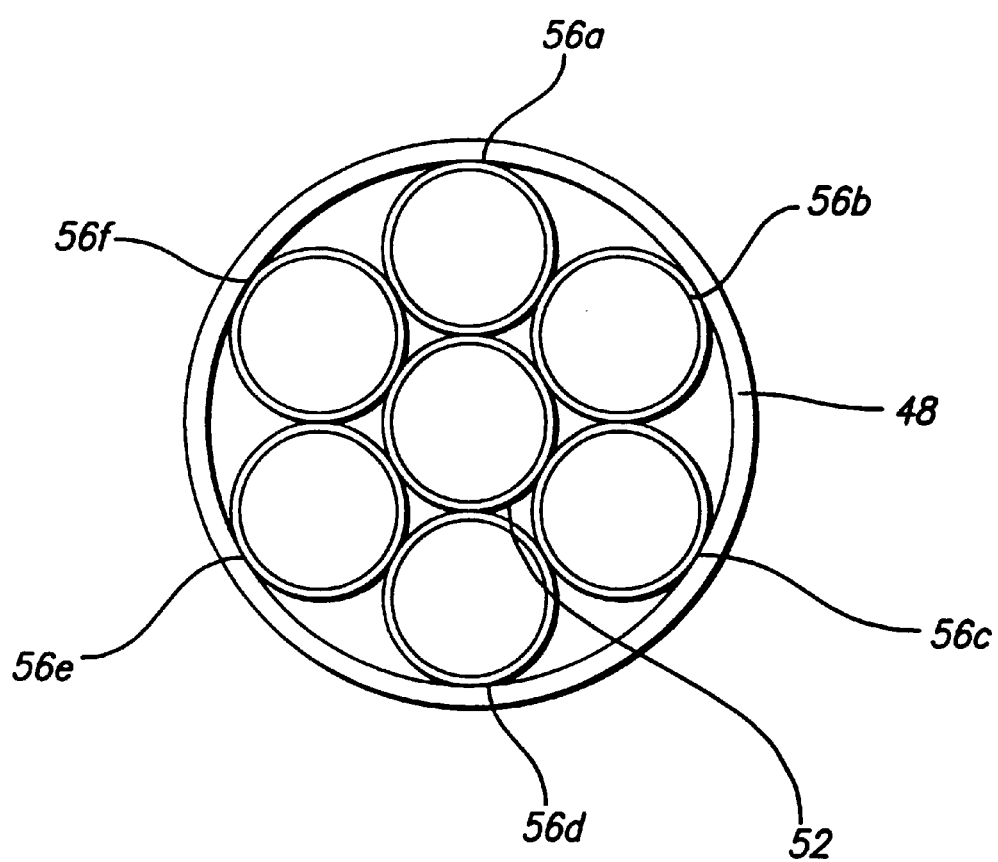
FIG. 15 is a distal end view of a fiber-optic bundle used in apparatus provided by the present invention.

Reference is now made to FIGS. 13–15 illustrating some of the apparatus formed in accordance with the invention for producing and detecting spectra indicative of the chemical composition of vulnerable plaques. FIGS. 13–14 provide illustrations of exemplary embodiments for analyzing tissue to detect vulnerable plaques in accordance with the invention. It should be appreciated that the detailed descriptions herein are presented for purposes of illustration and explanation, and accordingly, these embodiments are not to be considered as being limited to the particular applications described.

FIG. 13 schematically shows one embodiment of the apparatus 10 of the present invention. More particularly, the apparatus 10 includes a fiber-optic probe 12. The probe 12 includes an integrating sphere 14 of a type known in the art, and may be formed of any appropriate material. A compound parabolic concentrator (CPC) 18 is also mounted to the integrating sphere 14. The CPC 18 includes a main body member 20 formed from plastic and a polished aluminum lining 22. In addition, the CPC 18 also includes a central optical aperture 23 through which light may be directed and focused. This aperture preferably has a diameter between 0.64 and 0.84 mm, and more preferably of about 0.74 mm. A fiber-optic bundle 24 may be rigidly mounted to and held in an inlet port 26 in the integrating sphere 14, opposite the CPC 18. The fiber-optic bundle 24 (transmitting fiber-optic) may be operatively connected to a light source 30. The light source 30 may be particularly adapted for generating a spectrum of light having a wavelength range from 1400 to 4100 run, and more preferably from 1600 to 1800 nm. The light source 30 may, for example, be a tungsten-halogen lamp with wavelength selection being accomplished utilizing a concave holographic diffraction grating. Additionally, an individual light detector 34 may be mounted on the wall of the integrating sphere 14. Any appropriate detector(s) known in the art may be utilized including a lead sulfide detector and/or an indium antimonide detector cooled with liquid nitrogen. Light having a wavelength from about 1400 to 4100 nm, and more preferably from approximately 1600 to 1800 nm, from the source 30 may be directed simultaneously and in parallel along the transmitting fiber optic bundle 24 to the fiber-optic probe 12. There the light from the source 30 may be projected as an incident beam through the integrating sphere 14, the CPC 18 and the aperture 23 onto an arterial lesion or other tissue sample T (the incident light beam depicted in full line by action arrows A). Even scattered light of the incident beam may be redirected and concentrated by the CPC 18 so as to be tightly focused on a point P of the tissue sample T. A significant portion of the incident light projected onto the point P of the tissue sample T is reflected back into the CPC 18 through the aperture 23. The scattered or reflected light is shown in dash line with reference to action arrow B. As shown, the light may be directed by the parabolic walls of the CPC 18 into the integrating sphere 14. The integrating sphere 14 may then direct the light so that it falls upon the detector 34.

As shown in FIG. 13, the detector 34 may be connected to a means for analyzing the detected spectra 36 and producing color images thereof. Specifically, the analysis may be completed over the full wavelength range of the incident light directed upon the tissue. Thus, reflected or scattered light having a wavelength range between 1400 to 4100 nm, and more preferably from about 1600 to 1800 nm, can be analyzed sequentially within a bandwidth range of up to about 10 nm. Equal weighting may be also given to each wavelength in the analysis, unlike other methods. Hence, it should be appreciated that the present method may be distinguished from Fourier Transformation (FFT) or other data congression techniques like principal components (PCA). To achieve this end, computers may be utilized under the direction of appropriate analytical software such as the BEST Algorithm software program developed at the University of Kentucky by Robert A. Lodder. The BEST Algorithm software program calculates the distance of the spectrum of each point on the artery wall to the center of the distribution of an ordinary arterial wall. The user may select colors to denote directions of spectra in hyperspace, and hence the identity of chemical constituents. Thus, the direction may be color-coded to identify particular chemical species. Additionally, the length of the vectors (in standard deviations) is proportional to the concentration of the chemical species in the artery wall at the position where the spectra were recorded. Thus, the color images are actually color density-contour plots with contours that represent the mathematically determined probability of the tissue having a certain composition. The contours are drawn at set distances in standard deviations (SDs) from the spectra of a normal artery. As you go more and more SDs from normal, the probability of being normal (no excess LDL) is less. The relationship between SDs and probability can be looked up in a standard table of the Gaussian distribution. Previous SDs, such as Mahalanobis SDs, are generally based on the assumption that spectral clusters are normally distributed and have radial symmetry (either spheroid or ellipsoid). In contrast, the SDs of the BEST Algorithm are asymmetrical. In other words, the length of an SD is different in one direction than in the opposite direction. Accordingly, the SDs of the BEST Algorithm may be better suited to handle asymmetrical spectral distributions in hyperspace such as produced in complex mixtures like atheromas.

FIG. 14 illustrates an alternative embodiment 40 of the present invention. In this embodiment 40, the probe 42 includes a substantially cylindrical shaped housing 44. The housing 44 may be formed with a closed distal end 46 from any appropriate material including glass and, more preferably, zirconium fluoride glass. A fiber-optic bundle 48 may be rigidly mounted and held in an end cap 50 that seals the proximal end of the housing 44. Preferably, the end cap 50 is also made of glass that is, for example, heat welded to the sidewall of the cylindrical housing 44.

As shown in FIG. 15, the fiber-optic bundle 48 includes seven individual fiber-optic strands. A centrally disposed fiber-optic strand 52 (transmitting fiber-optic strand) may be operatively connected to a light source 54 (FIG. 14). The light source 54 may be similar to that described above with respect to FIG. 13. Six remaining fiber optic strands 56a–f (receiving fiber-optic strands) may be concentrically disposed about the central strand 52. Each of the receiving strands 56a–f may be operatively connected to an individual light detector 58a–f. Once again, any type of detector(s) 58a–f known in the art to be suitable for this purpose may be utilized (e.g. lead sulfide detectors and liquid nitrogen cooled indium antimonide detectors). An inverted, substantially conical reflector 60 may be mounted in the housing 44 adjacent the distal end 46. The reflector 60 may further include a parabolically curved sidewall specifically adapted for reflecting incident light (note full line action arrows C) outwardly through the sidewall of the optically pure catheterization housing 44 and focusing that light onto the surface of the arterial endothelium undergoing in vivo analysis. Scattered light reflected from the arterial endothelium may be directed by the substantially ellipsoidal sidewall of the reflector 60 back into the receiving fiber-optic strands 56a–f (note dashed line action arrows D). This light directing is furthered by having the distal end of the transmitting fiber-optic strand 52 extend a short distance (between 0.1 and 5.0 mm) beyond the distal ends of the receiving fiber-optic strands 56a–f as shown in FIG. 15. More specifically light is reflected downwardly from the outer sidewall of the transmitting fiber-optic strand 52 into the receiving fiber optic strands 56a–f. Further, each of the receiving fiber-optic strands 56a–f is effectively shaded from light reflected by the arterial endothelium at the opposite side of the artery. Hence, the resulting images may be clearer than would otherwise be obtainable. The fiber-optic strands 56a–f direct the reflected light to the cooperating detectors 56a–f to which the fiber-optic strands are respectively operatively connected. As indicated above with respect to the description of the embodiment shown in FIG. 14, the detectors 58a–f may be operatively connected to a supercomputer 62 that provides analysis of the spectra detected by the detectors and produces color images of the arterial endothelium. These images may be utilized to determine the chemical composition of the arterial endothelium and thus, the chemical makeup of any atherosclerotic lesions, and in particular, vulnerable plaques. Advantageously, by determining the chemical makeup of vulnerable plaques, a more effective treatment regimen may be promptly identified and initiated. As a result, the utilization of ineffective treatment regimens for the treatment of particular types of lesions may be avoided. Hence, less time is wasted in treatment and more effective and efficient treatment is provided for the improved safety and health of the patient at a lower cost.

In accordance with the methods of the present invention, in vitro analysis is also described herein with respect to the embodiment shown in FIG. 13. This may be done by excising and partially denuding a tissue sample from the endothelium of a portion of a artery or vessel wall. The excised tissue is incubated and washed. The tissue is then mounted on a micropositioning stage so that it may be carefully analyzed by passing beneath the optical aperture 23 of the CPC 18. As discussed above, the CPC 18 focuses simultaneously and in parallel a limited light spectrum having a wavelength from 1400 to 4100 nm onto a small spot on the tissue sample T. More preferably, the light spectrum may have a wavelength range from 1600 to 1800 nm that may be referred to as one water window. Major spectral changes indicating the presence of low-density lipoprotein (LDL) may be observed in this range. In order to determine the presence of these low-density lipoproteins with analytical precision, it may be necessary to utilize light across the appropriate spectrum indicated. The spectra may be scanned within the water window between 1650 and 1780 nm, where LDL cholesterol is generally known to have two major peaks, or around 2080 nm, where thin caps may have characteristic peaks. These and other selected water windows may thus provide a selected range in which distinctive absorbance patterns or signatures of plaque constituents can be imaged even in the presence or through blood, and provide a series of one or more markers for vulnerable plaques. However, most tissue absorbs light at all wavelengths across a wider range, and different tissues absorb only a little more at some wavelengths than others. When the particular wavelength(s) where these differences occur are not known in advance, it may be preferable to analyze the entire range with each wavelength being given equal weight in the analysis. Further, this may be done simultaneously and in parallel to provide a speed of imaging suitable for clinical applications. It may be thus possible to avoid missing the presence of unusual tissue of interest to the clinician completing the study. As indicated above, the reflected or scattered light may be analyzed using computers with sufficient processing power that are operatively controlled by appropriate software.

In accordance with a further aspect of the present invention, methods are further provided for analyzing arterial endothelium in vivo utilizing the apparatus, for example, as shown in FIGS. 14–15. The probe 42 may be first introduced into an artery. This may be done by any known procedure appropriate for this purpose involving incision and opening of a portion of the artery for placement of the catheter probe 42 therein. Procedures similar to those used for the completion of angioplasty operations may be used for this purpose. After introducing the probe 42 into the artery, the probe may be manipulated until it is positioned to allow analysis of the desired portions of the arterial endothelium. This positioning may be again completed in accordance with standard techniques utilized in angioplasty procedures. Once the probe 42 has been properly positioned, the method continues with the step of continuously focusing simultaneously or sequentially, and in parallel, the near-IR spectrum from about 1400 to 4100 nm, or more preferably from about 1600 to 1800 nm, onto the entire area of arterial endothelium to be analyzed. Next, is the detecting of the light reflected or scattered by the arterial endothelium by the detectors 58a–f. In addition to analyzing the very thin endothelium, the technique permits analysis of the contents located deeper within the arterial wall. Finally, the method may conclude with the step of analyzing the spectra detected from the arterial endothelium and producing color images thereof. More specifically, the full spectrum range of light originally focused upon the arterial endothelium may be detected simultaneously and in parallel, and then analyzed simultaneously and in parallel. During the analysis, equal weighting may be given to each wavelength so as to insure that any variations in absorbance at any wavelength for each location of tissue undergoing analysis is observed. Alternatively, a more limited spectrum range or water window may be analyzed when particular peaks are known to occur with vulnerable plaques and constituents thereof including fibrous caps and lipid pools. Reference plaque samples may provide spectra that are associated with indexes or characteristics of plaque vulnerability including thin caps, lipid pools, and macrophages by histology. These spectra may then be sought using pattern recognition in a validation set of unknown samples. Moreover, the present method and apparatus spatially provide chemical analysis resulting in the production of color images that allow a doctor or a lab technician to determine the location and quantities of substances such as high density lipoprotein (HDL), low density lipoprotein (LDL), and apolipoproteins, such as apoA-I, apoA-II and apoB, in living arterial tissue. High speed parallel data acquisition and analysis of arterial lesions are thus achieved in vivo. In particular, accurate and prompt analysis of vulnerable plaques in vivo is a very important advance in the art as these types of lesions may be treatable and may warrant appropriate therapies to promote their stability with drugs or other treatment. This method allows vulnerable plaques to be identified by type, and in some cases, may avoid unnecessary surgery for lesion bypass. Excessive time may be thus avoided to undergo ineffective or inapplicable drug treatments.

The ability to perform prospective identification of vulnerable plaques as described herein advantageously provides many opportunities to understand their make-up and the ability to perform kinetic experiments in which the quantities of lipoprotein and apolipoprotein substances are studied over time in these lesions. This may be done both as the lesion grows and/or as various cholesterol-lowering drugs are administered in attempts to shrink or stabilize the lesion. In summary, numerous benefits have been described which result from employing the concepts of the invention. The described apparatus and methods may be utilized to effectively and efficiently determine the chemical composition of vulnerable plaques in a real-time or substantially near real-time manner. These procedures may be also completed either in vitro or in vivo, and are particularly adapted for promptly determining the makeup of vulnerable plaques as found in the inner walls of arteries.

C. Near-IR Therapy and Stabilization of Vulnerable Plaques

The methods and apparatus described above may be readily modified to provide near-IR laser therapy to stabilize plaques that are identified as vulnerable. For example, when the spectra from a lesion indicates the presence of a thin fibrous cap covering a lipid pool, near-IR laser energy may be applied through the same or different catheter to promote fibrosis. Thickening the fibrous cap on the plaque may be achieved to prevent rupture and leakage of the lipid pool into an arterial lumen. Data obtained from human skin in volunteers demonstrate that a high power Nd:YAG pulse (>100 mJ) of less than 10 ns duration causes tissue calcification. This effect may further provide another possible treatment for the stabilization of vulnerable plaques that are identified using the near-IR catheter systems provided herein.

III. Research Design and Methods

The present invention further provides an overall system consisting of various steps that may be developed over a defined period of time for detecting and identifying a variety of vulnerable plaques in arterial blood vessels including the coronary arteries.

A. Overview of Research Design

The general methodology prescribed by the invention may progress for additional validation of the near-IR method through a series of Specific Aims by initially identifying vulnerable plaques in human autopsy specimens (Specific Aim #1), testing of near-IR catheters systems in vivo in rabbits with vulnerable plaques (Specific Aim #2), and eventually to the introducing their use with patients for in vivo vulnerability detection (Specific Aim #3) as part of an overall effort to construct a near-IR mapping of the coronary tree (Specific Aim #4). It should be noted that imaging in humans may be accomplished while studying a group already undergoing intervention that has a high risk of adverse events, even after a successful procedure, wherein the IR imaging will add minimal risk. The detection of a vulnerable plaque may indeed help stratify risk, and provide the opportunity to enter further studies and a possible therapy. A particular goal for such a study may include the comparison of the near-IR map of the human coronary obtained in 600 patients with the expected 80 coronary events that will occur during the year of follow-up. These types of relationships may be used to calibrate and to validate a prospective near-IR index of vulnerability.

B. Timetable

Specific Aims 1 and 2 may be accomplished during year 1. Specific Aim 3 may begin in Year 2 and continue until the end of the year 4. Follow-up after year 4 may continue. Analysis for Specific Aim 4 may also begin in year 3 as sufficient follow-up data emerges.

C. Specific Aim #1—Validation in Autopsy Specimens

1. Overview

The Pathology Department at the University of Kentucky Hospital performs about 240 autopsies per year, 30% of which are for cardiac related deaths. Human aortas and coronary arteries may be evaluated and dissected from these cases in the cardiac pathology laboratory. During year 1; for example, 30 samples from each aorta and each coronary tree of ten adult necropsies will form the basis for near-IR/ Histologic calibration and validation. The autopsy samples may be analyzed in order to collect near-IR spectroscopy data in a blinded manner, and then returned to the cardiac pathology laboratory for morphologic and morphometric studies to identify plaque vulnerability. Data from the histologic studies is correlated with near-IR data and subjected to statistical analysis.

2. Detailed techniques

Macroscopic evaluation of the fresh aorta at the time of autopsy allows for systematic sampling of a region of the descending aorta from 2 cm distal to the origin of the left subclavian artery to the level of the renal arteries. Two parallel circumferential zones (10 mm wide by 45 mm in length), decalcified as necessary after immediate specimen X-ray (Faxitron system) was taken in the transverse plane from the opened aorta. The 45 mm by 10 mm strip of aortic tissue was subdivided into thirty 1.5 mm by 10 mm tissue blocks and imaged along the intimal surface by near-IR to generate individual-block specific spectroscopy data as described in preliminary data. Epicardial coronary arteries were carefully removed fresh, decalcified as necessary after immediate specimen X-ray, serially cut into 5 mm blocks, and similarly submitted for near-IR imaging as described in Preliminary Data. After imaging, each tissue block was labeled, fixed in formalin and processed into paraffin for histologic evaluation and morphometry. Elastic trichrome combination stain of 5 micron thick oriented sections on glass slides identified the microscopic topographic features of the intima, media and adventitia of normal and atherosclerotic vessel as described previously (Abela G S, Picon P D, Friedl S E et al, Triggering of plaque disruption and arterial thrombosis in an atherosclerotic rabbit model, Circ 1995; 91:776–84). Independent observers evaluated each coded slide for histologic features of plaque vulnerability such as: (1) a thin fibrous cap defined as less than 65 microns in thickness; (2) a large lipid pool defined as a lipid pool greater than 30% of the total cross sectional area of the plaque by computerized planimetry; and (3) an increased ongoing inflammation defined as macrophage infiltration greater than 10% of the total area of the plaque by computerized planimetry. The light microscopy and morphometry of prepared slides was performed using an existing Olympus OMX double-headed microscope equipped with 2× up to 65× (high dry) objectives digitally interfaced to an automated multiphasic quantifying videoscreen morphometry system (Quantum Zedex with Accuvue 21 inch monitor). Quantitation of fibrous cap thickness was performed on parallel serial sections stained by the elastic trichrome combination technique. Quantitation of lipid pool was also performed on parallel serial sections stained with Sirius Red for collagen. The non-staining lipid pool contrasts with the highlighted collagen using a green filter. Quantitation of macrophage infiltrate was evaluated by immunohistochemistry using pan-macrophage antibody 7.6 ug/ml anti CD-68; KP-1 (M814 DAKO Carpinteria, CA) and the biotin-streptavidin amplified detection system developed with peroxidase-DAB.

3. Statistical Analysis

Near-IR spectroscopy and histology classified each of the aortic and coronary segments for the presence or absence of a thin fibrous cap, large atheromatous core and macrophages. A correlation between near-IR spectra and histologic data may be formulated using histology as the gold standard for presence (true positive) or absence (true negative) of these three variables. Plaque may be classified as "vulnerable" or "not vulnerable." Near-IR spectroscopy sensitivity, specificity, accuracy, positive predictive value, and negative predictive value, for each component of vulnerable plaque and for overall vulnerability may be thus calculated.

D. Specific Aim #2—Vulnerable Plaque Detection by Catheter in Rabbits with Diet-Induced Atherosclerosis.

This study tests the hypothesis that near-IR spectroscopy can identify vulnerable plaques in the aorta of atherosclerotic rabbits in vivo.

1. Materials and Methods.

Twenty New Zealand rabbits fed a 1% cholesterol diet may be utilized. These rabbits are fed with alternating cycles of 1% cholesterol diet for four weeks followed by normal diet for four weeks. This model of prolonged, pulsed feeding produced rabbits with lesions extremely similar to advanced plaques in humans (Constantinides P, Chakravarti R N, Rabbit arterial thrombosis production by systemic procedures, Arch Pathol 1961; 72:197–208). Individual rabbits will have vulnerable plaques, fibrous plaques, fatty streaks, and normal aorta, thus providing a range of targets for imaging. Rabbits may be anesthetized with atropine sulfate as a preanesthetic (0.1 mg/kg, i.m.) followed by ketacet (35 mg/kg, i.v.) and xylazine (5 mg/kg, i.v.). With the rabbit anesthetized, an incision near the femoral artery will provide access to the aorta. The catheter, which will be utilized in the human coronary studies, will be inserted into the femoral artery. It may be a relatively small diameter fiber-optic bundle with a prism at the tip to direct light, and collect reflectance from the adjacent arterial wall. It may be also connected to a tunable laser, a detector, fast A/D, and computer. The laser should provide enough light to obtain usable spectra through the blood and endothelial tissue. The catheter may be advanced to the thoracic descending aorta, where near-IR images of the arterial wall may be made. Using the carotid artery for access, an angiographic catheter will be advanced retrograde to the ascending aorta for simultaneous angiography. A cineangiogram may be recorded during pull-back to align the near-IR image with subsequent histologic section. Angiographic landmarks and fluoroscopy may identify the exact area of initial registration, immediately after the take-off of the subclavian artery. The near-IR spectroscopy catheter may be withdrawn using automatic pullback with further registration every 10 mm in the descending aorta until the aortic bifurcation. With the catheter fixed in position, the animal will be euthanized by an overdose of anesthetic (Pentobarbital 120 mg/kg IV), and the aorta dissected with the catheter in place. A suture tied on the catheter will permit final measurements for proper registration. The portion of the aorta scanned by the near-IR catheter (thoracic descending and abdominal aorta, immediately after the take-off of the subclavian artery until the bifurcation) will be removed and analyzed by histological and immunocytochemistry techniques for correlation with the results of near-IR spectroscopy. The histologic features of the vulnerable plaque, as defined by Burke et al (Farb A, Burke A P, Tang A L et al, Coronary plaque erosion without rupture into a lipid core: A frequent cause of coronary thrombosis in sudden coronary death, Circulation 1996; 93:1354–63) and enumerated in Specific Aim 1 will also be utilized to identify these plaques in the rabbit study.

2. Histological Analysis

Cross-sectional tissue samples (1 cm in length) may be taken from circumferential aortic segment aligned with near-IR vulnerable sites and analyzed as in Specific Aim 1.

3. Statistical Analysis

Correlations between near-IR signs of vulnerability and histologic evidence of vulnerability may be established in the same manner as Specific Aim 1.

E. Specific Aim #3 —Vulnerability Detection and Follow-Up

1. Overview

This study utilizes a near-IR coronary catheter capable of determining the chemical composition of coronary arteries. The catheter may be used in a group of 600 patients undergoing PTCA/stenting of the coronary arteries. A primary goal of this specific aim is to obtain the near-IR map of the coronary arteries, and correlate the initial images with subsequent coronary events. both angiographic and clinical. This relationship will be used to broaden the near-IR definition of plaque vulnerability beyond the near-IR recognition of lipid pools and thin caps, the characteristics generally referred to in this application for vulnerable plaques.

Since near-IR imaging involves some small risk to patients there should be off-setting benefits. For this reason, patients identified to have a vulnerable plaque by near-IR are offered the opportunity to participate in a pilot study of an agent that might stabilize such a plaque. For example, given the evidence that MMP may contribute to plaque vulnerability, it is possible that inhibition of these proteases would be beneficial. An MMP inhibitor has already been developed (Agouron Inc.) and has been shown thus far to be relatively safe in early studies in patients with prostate cancer. Moreover, an oral inhibitor of sPLA2 has also been developed. A variety of other agents may be also selected for various applications. A randomized study with only 100 patients alone may not have sufficient power to completely detect a beneficial effect of therapy. However, studies may provide data for a definitive trial, and provide the potential benefit to individual patients to off-set the low risk of near-IR imaging.

2. Safety of the Near-IR Imaging Technique

The risk of near-IR imaging may be similar to that of ICUS, which is less than 0.1% for a major complication.

3. Patient Population a) Location of Study

Subjects to be enrolled in the study may be recruited from patients scheduled for PTCA/stenting at facilities such as the Cardiac Catheterization Laboratory of University of Kentucky Hospital. This laboratory performs approximately 300 of these procedures annually, providing a sufficient population from which we will be able to recruit patients. The patient population is approximately 60% male, and 10% minority.

b) Eligibility and Informed Consent

Patients are able to give informed consent, and are older than 30; and less than 75 years of age. They are selected by their treating physician to receive PTCA/stenting for routine clinical indications. Informed consent for near-IR imaging and possible entry into the randomized clinical trial (if a vulnerable lesion is detected) may be obtained at the same time. Patients may also be asked at enrollment to consent to a 1-year follow-up catheterization if a vulnerable near-IR image is detected.

c) Baseline Data Collection

Data pertinent to the existence, and possible progression of vulnerable lesions may be collected on standardized data forms. Data will include age, gender, race, education level, medical history, smoking and estrogen status, and history of CAD. A full lipid profile may also be determined.

Because of the know potentiation of sPLA2 by serum amyloid A (Pruzanski W, de Beer F C, de Beer M, Stefanski E, Vadas P, Serum amyloid A protein enhances the activity of secretory non-pancreatic phospholipase A2; Biochem. J 1995; 309:461–4), a blood sample may be drawn for determination of this plasma constituent. CRP will also be measured. The sample may be frozen and retained for future studies of plasma factors not currently recognized to be related to plaque rupture. 4. Proposed Initial Near-IR Imaging After passage of a 0.014 inch guide wire, the culprit lesion may be first dilated and/or stented. Then the near-IR catheter may be advanced over the wire past the culprit lesion to the most distal portion of the artery that still has an angiographic diameter exceeding 2 mm. Once the near-IR catheter is in place, an automated pullback device may be used to maintain withdrawal of the catheter at a fixed rate. Near-IR data may be recorded in registration with cineangiographic data demonstrating the location of the radio-opaque tip of the near-IR catheter. This will make it possible to match individual sites within the coronary artery with the near-IR images. Angiographic and fluoroscopic landmarks such as side branches may also be used to assist in identifying the arterial segment over which the catheter has been retracted. After the vessel undergoing PTCA has been imaged, the remaining major coronary arteries (proximal angiographic diameter exceeding 3 mm) may be entered with a guidewire, and near-IR imaging performed in a manner identical to that performed in the artery receiving PTCA/stent treatment. Additional vulnerable plaques that are identified may be further stabilized by stenting or other alternatives described herein in accordance with the invention.

5. Method of Randomization

After consent and enrollment, and identification of a vulnerable lesion by near-IR, patients may be randomized in standard manner to placebo or active MMPI therapy. Therapy may begin within 12 hours after the vulnerable lesion is detected. The primary analyses may be based on intention-to-treat.

6. Follow-up a) Patients with a Near-IR Signature of a Vulnerable Plaque

These patients, estimated to number about 100; may be randomized to an MMP inhibitor, or placebo, maintained on blinded therapy for 1 year. Patients in both groups may also receive maximum secondary prevention therapy, as indicated by their clinical condition, including aspirin, and intensive lipid lowering therapy with a goal of LDL lower than 100 mg/dl. They may then return for diagnostic catheterization with near-IR mapping to determine if the near-IR signs of vulnerability persist. If an interim clinical event occurs (death, MI, need for repeat revascularization) prior to 1 year, efforts will be made to obtain an additional IR map at any catheterization required, and perform post-mortem study of the heart in cases of death. If vulnerability persists at 1 year, the patients may be randomized to a second treatment, probably an sPLA2 inhibitor, and catheterized at year 2.

b) Patients with No Near-IR Evidence of a Vulnerable Plaque

It is expected that about 500 patients will have no evidence of vulnerability. These individuals may be contacted by telephone at 6 month intervals to determine the incidence of clinical events, which will be treated in an identical manner to those in the patients with vulnerability by near-IR. An important endpoint may be the ability of near-IR imaging to risk-stratify the 600 patients into groups with high and low risks of clinical events at 1 year, and beyond.

c) Follow-up beyond 1 year

All patients who have a near-IR map obtained may generate valuable information when events occur, even after 1 year post-randomization. Hence, 6 month telephone contacts may be continued with all patients after the 1 year follow-up.

7. Assessment of Angiographic Endpoint

The University of Kentucky catheterization laboratory has an advanced General Electric system with digital storage of angiographic images. This system may be used for blinded, quantitative comparison of initial and follow-up angiograms obtained in identical views at the two points. For each lesion, the single view showing the most severe degree of stenosis may be used for analysis. Percent stenosis and reference diameter may be determined using the guiding catheter filled with contrast for calibration and a digital quantitative coronary analysis computerized program.

8. Examination of the Heart in Patients who Die Following Near-IR Mapping

The small number of patients who may die following near-IR mapping (6 deaths are expected in 1 year in the 600 undergoing imaging) may provide an invaluable opportunity for the correlation of near-IR images obtained in vivo with histologic findings. Efforts may be made to obtain at least a "heart only" autopsy in each instance.

9. Data Collection and Database Management

All data may be entered onto prepared worksheets at the time of data collection. Quality control may be maintained by automatic range checking of all variables, double entry from forms to the computer, and automated comparison of the two resulting databases, with any discrepancies being manually verified.

10. Statistical Analysis.

a. Identification of Patients with Vulnerable Plaques

In 600 patients undergoing PTCA/stenting, near-IR imaging may be performed to screen for the presence of non-disrupted vulnerable plaques. An estimate of the percent of patients in whom such plaques may be detected may be based on prior experience (screening with ICUS and angioscopy) and autopsy studies. In prior studies conducted at the Deaconess Hospital in Boston (conducted by Dr. James Muller), angioscopy and ICUS were utilized in an attempt to identify non-disrupted potentially vulnerable lesions in patients with culprit lesions in other locations in the vessel. Using these less sensitive measures (yellow color by angioscopy, and large hypoechoic area by ICUS), 7 such lesions were encountered when examining a single artery in each of approximately 200 patients (3.5%). With imaging of 3 vessels, it may be anticipated that the frequency may increase to 10% with these measures which are likely to be less sensitive than near-IR imaging. However, autopsy studies have reported a much greater frequency of non-disrupted vulnerable plaques, and disrupted vulnerable plaques not causing clinical symptoms. Burke et al have reported that at least 80% of patients dying suddenly have a vulnerable plaque in addition to the culprit lesion (Burke A P, Farb A, Malcom G T, Liang Y-H, Smialek J, Virmani R, Coronary Risk Factors and Plaque Morphology in Men with Coronary Disease who Died Suddenly, N Engl J Med 1997; 336:1276–82). However, it is possible that patients dying suddenly have far more vulnerable plaques than those that survive to undergo PTCA/stenting. Therefore, to avoid possible overestimation of the frequency of vulnerable plaques in the population to be studied (with estimates running from 80% in autopsy studies to 10% by ICUS and angioscopy) a conservative estimate of 16% may be chosen, yielding 100 patients for the vulnerable group. If vulnerable plaques are more frequent than 16%, the goals of the project may be more easily attained. The 100 patients may be randomized to stabilization therapy or placebo, and a repeat angiogram and near-IR map may be obtained a year later. Clinical events (death, MI, revascularization) can also be monitored.

b) Analysis of Risk Stratification

A primary statistical goal of Specific Aim 3 is to determine the ability of the near-IR catheter to identify a group of patients at a high risk of a subsequent clinical event. Clinical events will be the composite of all-cause deaths, myocardial infraction, and revascularization. The event rate for a clinical event may be higher in the vulnerable group than non-vulnerable group. The rate of the composite clinical endpoint may be compared between the vulnerable and non-vulnerable groups, using chi-square tests. Life-table analysis with the product-limit methods may be also used to estimate event rates at 1 year. Cox regression models may be used to estimate crude and adjusted relative risks of clinical events.

c) Expected Numbers of Clinical and Angiographic Events

The clinical event rates for patients undergoing PTCA/stenting have been well-described. Colombo et al reported follow-up results in a group of 890 patients undergoing stenting, similar to those in the proposed study (Colombo A, Di Mario C, Reimers B, Blengino S, Akiyama T, Ferraro M, Martini G, Di Francesco L, Finci L, Coronary stenting in 1000 consecutive patients: Long-term clinical and angiographic results, G Ital Cardiol 1997, 27(1):19–31). At a mean interval of 14 months post-stenting, rates were 10% for PTCA for de novolesions, 3.7% for CABG, and 4.7% for death. On the basis of these, and similar data in the literature, conservative estimates for the clinical event rate within 1 year may be 1% death, 4% MI, 4% CABG, and 4% for revascularization of a lesion other than the original target lesion. Considering some overlap, this may yield a composite event rate of 10%. If the patients with vulnerable plaques had twice the probability of developing an adverse event, the expected rate of a composite clinical event would be approximately 20% during one-year follow-up. 20 events in the group with vulnerable may be expected versus 50 events (8%) in the group without vulnerable plaques. The power of the study to detect an absolute difference of 12% in clinical events in the vulnerable group versus the non-vulnerable group at the $p<0.05$ level would be about 0.89.

An angiographic event or development of rapid plaque progression, defined as a new complete occlusion and/or a >20% absolute increase in stenosis, may be monitored by comparing initial to the 1 year of follow-up angiogram. The rate of rapid progression of coronary lesions has been determined in 295 patients on a waiting list for PTCA in England. Over an 8 month follow-up 42 patients (14%) experienced an increase in stenosis of >20% and/or a new total occlusion, at sites not designated as culprit lesions. The progression rate was higher in patients with a stabilized acute coronary syndrome, than in those with stable angina, as the indication for revascularization. (Kaski J C, Chen L, Crook R, Cox I, Tousoulis D, Chester M R, Coronary stenosis progression differs in patients with stable angina pectoris with and without a previous history of unstable angina, Eur Heart J 1996; 17:1488–94; Chen L, Chester M R, Crook R, Kaski J C, Differential progression of complex culprit stenoses in patients with stable and unstable angina pectoris, J Am Coll Cardiol 1996; 28:597–603). On the basis of these, and similar data in the literature, conservative estimates for rapid progression may be about 20% for 1 year versus 14% for 8 months noted above.

Based on the above assumptions, the expected numbers of angiographic plus clinical events during 1 year of follow-up would be:

|  | Clinical Events | Additional Angiographic Events | Total # of Events |
|---|---|---|---|
| With vulnerable plaques, n = 100 | 20 | 20 | 40 |
| Without vulnerable plaque, n = 500 | 40 | 0 | 40 |
| Total Study Sample, N = 600 | 60 | 20 | 80 | d) Secondary Analyses for Randomized Pilot Study

The clinical and angiographic events in the MMPI pilot study may be both monitored. However, the sample size may be insufficient to detect a beneficial effect unless it is of considerable magnitude.

F. Specific Aim #4—Near-IR Mapping of the Coronary Tree

1. Overview

The overall near-IR map of the 3 major coronary arteries obtained during screening may be used to prospectively characterize all segments likely to lead to a major coronary event. The need for such an approach may be based in part to the lack of certainty that vulnerable plaques (which may be generally characterized by a lipid pool, thin cap, and inflammation) are the segments of the coronary most likely to produce subsequent disease. For instance, sites prone to plaque erosion (as opposed to rupture) leading to thrombosis, may not be identified by near-IR signs of lipid and thin cap. The power of near-IR spectrometry may be therefore utilized to make a complete chemical inventory of the coronary tree for subsequent examination after a coronary event has occurred. Thus, each clinical event (death, MI, unstable angina associated with a discrete lesion) and each angiographic event (rapid progression) may produce a site proven to be vulnerable.

In addition to the 100 patients with vulnerable plaques, this analysis may include the 500 patients who are screened, but not found to have the near-IR signs of vulnerability. Follow-ups may be performed with these patients with bi-annual telephone contact to determine if clinical events occur. If events occur, the location of the culprit lesion may be determined by clinical data, angiography and/or autopsy. As described in Specific Aim #3; it may be expected that about 80 patients may develop clinical or angiographic events. The 40 events expected in the first half of the study may be used to construct a multi-variate near-IR vulnerability index that may be prospectively validated for its ability to predict events in the second half of the study.

2. Near-IR Library Describing the Chemical Composition of the Arteries

An enormous quantity of information may be available in the near-IR images recorded at baseline. The estimated size of the database may be about 41.5 gigabytes. This information may be stored on computers such as the University of Kentucky supercomputer (an HP SPP2000). From this repository, it is possible to analyze the near-IR signal from the sites proven to progress in two ways: (1) Analysis of known compounds and microanatomy at the vulnerable site—the near-IR signals of compounds such as cholesterol, LPC, FFA and the thin cap, lipid pool plaques will be analyzed as univariate and multi-variate predictors of rapid progression; and (2) Comparison of the near-IR signal of sites that progress versus those that do not—through this methodology, new causes of plaque vulnerability may be identified.

3. Statistical Analysis

Because of the enormous quantity of information contained in near-IR spectra, specialized statistical techniques have evolved for their analysis. The following is a brief summary of the approach. Details are found in known references in the subject area and the art. The BEST (Bootstrap Error-Adjusted Single-Sample Technique) may be used to construct chemical composition maps. It calculates distances in multidimensional asymmetric nonparametric central 68% confidence intervals in spectral hyperspace (roughly equivalent to standard deviations). The BEST metric can be thought of as a "rubber yardstick" with a nail at the center (the multidimensional mean). The stretch of the yardstick in one direction is therefore independent of the stretch in the other direction. This independence enables the BEST metric to describe odd shapes in spectral hyperspace (spectral-point clusters that are not multivariate normal, like the calibration spectra of many biological systems). BEST distances can be correlated to sample composition to produce a quantitative lipoprotein calibration, or simply used to identify regions with lipoprotein distributions similar to plaque in a spectral image. The BEST automatically detects samples and situations unlike any encountered in the original calibration, making it more accurate in biomedical analysis than typical regression approaches to near-IR analysis. The BEST also produces accurate distances even when the number of calibration samples is less than the number of wavelengths used in calibration, in contrast to other metrics that require matrix factorization. In addition, the BEST retains the direction vector of a standard deviation in hyperspace throughout all calculations, an essential characteristic for multi-component quantification of sample composition. The BEST further calculates the integral of a probability orbital in hyperspace by starting at the centroid of the orbital and working outward in all directions at a uniform rate. The distance between the center of a plaque orbital and a sample spectrum is proportional to the concentration(s) of the plaque constituent(s) responsible for the vector connecting the central and sample-spectral points. The direction of the vector identifies the constituent(s) of the plaque. The BEST direction and distance are typically used to create color contour plots of the spatial distribution of lipoproteins. In such plots, the contours are drawn at sequential distances in SD's, and RGB (red-green-blue) colors are used to denote class membership based on vector direction. The intensity of the color is proportional to the amount of substance present. Shades of blue are used to represent sample spectra similar to those already in the calibration set, while shades of red are used to represent sample spectra that contain the selected analyte. Shades of green are used to represent a second analyte or possible interfering effect. The BEST offers improved performance as an assimilation method or a method that progressively increases its analytical performance by incorporating previously unknown samples into its calibration. The calibration samples are analyzed by another reference method such as those listed earlier in the same manner that Beer's Law is used to develop a conventional spectrophotometric calibration.

In the BEST, a population P in a hyperspace R represents the universe of possible spectrometric samples (the rows of P are the individual samples, while the columns are the independent information vectors, such as wavelengths or energies). P* is a discrete realization of P based on a calibration set T, which has the same dimensions as P* and is chosen only once from P to represent as nearly as possible all the variations present in P. P* is calculated using a bootstrap process by an operation (T), and P* has parameters B and C, where C=E(P) and B is the Monte Carlo approximation to the bootstrap distribution. The expectation value, E( ), of P is the center of P, and C is a row vector with as many elements as there are columns in P.

Each new sample spectrum X is analyzed by an operation (T,B,X,C) (Toussaint J-F, LaMuraglia GMS J F, Fuster V, Kantor H L, Magnetic resonance images lipid, fibrous, calcified, hemorrhagic, and thrombotic components of human atherosclerosis in vivo, Circ. 1996; 94:932–8), which projects a discrete representation of the probability density of P in hyperspace by many-one mapping onto the vector connecting C and X. X and C have identical dimensions. The directional standard deviation (SD) is found from the projected probability density in Equation 1.

$$\left\{ \sigma \left| \frac{\int_\Omega^\sigma \left( \int_R P* \to \vec{CX} \right)}{\int_R P* \to \vec{CX}} = 0.68 \right. \right\}$$

Equation 1

The integral over the hyperspace R is calculated from the center of P outward. The calculation of a skew adjusted (is based on a comparison of the expectation value C=E(P) and C=med(T), the median of T in hyperspace (with the same dimensions as C) projected on the hyperline connecting C and X in Equation 2.

$$(C-C_T) \to C\vec{X}$$

Equation 2

The result of the corrected projection is an asymmetric that provides two measures of the standard deviation along the hyperline connecting C and X:

$$\left\{ +\vec{\sigma} \left| \frac{\int_\Omega^{+\sigma} \left( \int_R P* \to \vec{CX} \right)}{\int_R P* \to \vec{CX}} = 0.34 \right. \right\}$$

Equation 3

$$\left\{ -\vec{\sigma} \left| \frac{\int_\Omega^{-\sigma} \left( \int_R P* \to \vec{CX} \right)}{\int_R P* \to \vec{CX}} = 0.34 \right. \right\}$$

Equation 4

Equation 3 in the direction of X in hyperspace, and Equation 4 in the opposite direction along the hyperline connecting C and X. Skew adjusted SDs can be used to calculate mean distances between spectra of different samples.

The supercomputer used to run the BEST may be a 64 processor Hewlett-Packard Exemplar SPP2000 system with 30 gigabytes of memory and 300 gigabytes of disk storage. The speed in the BEST is projected at 51.2 Gflops for the system based on current data from the SPP 1200. Chemical composition maps of the coronary tree may be analyzed on a Pyramid Systems ImmersaDesk.

IV. Human Subjects

Subjects to be enrolled in these studies may be recruited from patients scheduled to undergo percutaneous transluminal coronary angioplasty (PTCA) at a facility such as the Cardiac Catheterization Laboratory of University of Kentucky Hospital. The laboratory performs approximately 300 coronary interventions per year. The percentage of female patients is approximately 25%, and minorities are 10%. The investigators may further attempt to recruit female and minority subjects into the proposed study. The age range of subjects may be between 30 and 75 years of age. All patients will have been diagnosed with coronary artery disease by coronary angiogram prior to the proposed studies. Exclusion criteria will include: 1) acute myocardial infarction (during the first 24 hours); 2) severe congestive heart failure; 3) cardiogenic shock; 4) left ventricular ejection fraction <40%; 5) aortic stenosis with aortic valve area <0.8 cm2; 6) pregnancy; 7) prisoners.

As mentioned above, potential study subjects may be identified from patients scheduled to undergo PTCA/ stenting. A physician investigator or the research nurse may approach the patient, explain the procedure and obtain consent if the patient meets eligibility criteria as previously described. IRB approval for the procedures may be applied for, and an IRB-approved consent form may be thus used. Sources of research material obtained from individually identifiable living human subjects may include clinical data from the hospital chart, angiographic data from the catheterization laboratory and near-IR spectroscopy data collected at the time of catheterization. Specimens would not have to be collected.

The risks to patients incurred as a consequence of participating in this project are related to the performance of near-IR imaging, and the drugs to be studied. The photon energy delivered by near-IR to the wall is well below the energy levels that produce either thermal or ionizing harmful effects. Hence, the safety of near-IR imaging of arteries may be more dependent upon the risk of catheter manipulation. Since the near-IR catheter is quite similar in size and flexibility to an ICUS catheter, and because neither requires coronary occlusion, the risks of the near-IR method may be similar to those of ICUS. There is extensive literature available regarding the use of guide wires and ICUS as is known in the art. It was reported from a multi-center survey of the use of 2207 ICUS procedures that coronary spasm was the most frequent event, and occurred in 2.9% of the procedures. All episodes of spasm were benign, and none were associated with major complications. Acute procedural complications other than spasm, included dissection, air embolism, acute occlusion and thrombus formation, and occurred in 0.3% of procedures. Major complications occurred in only 0.1% of the ICUS studies (Hausmann D, Erbel R, Alibelli-Chermarin M J et al: The safety of intracoronary ultrasound, A multi-center survey of 2207 examinations, Circ. 1995; 91:623–30). Individual patients may further benefit from participation in the study, and may receive improved information on the risk of their condition (from near-IR imaging), and a decrease of that risk by treatment with an MMP and/or a sPLA2 inhibitor as described above.

V. Vertebrate Animals

The proposed animal work may be performed with New Zealand rabbits as described above in accordance with the invention. These rabbits may be fed a sequence in which a cholesterol enriched diet is fed for 2 months, followed by return to normal laboratory diet for 2 months. This sequence may be repeated twice. This is an established dietary regimen that is well tolerated by the rabbits. Only same-sex groups will be compared for atherosclerosis. The ages of the rabbits will be approximately 3 months at the initiation of the study. An estimated 20 rabbits may be needed for completion of such a study. Rabbits have been extensively used for atherosclerosis research, and may be the smallest animal that may used for validation of catheter based near-IR imaging studies. The numbers outlined are based on realistic estimates of those needed to complete the experiments outlined and on the numbers required to produce statistically robust data on the extent of atherosclerosis.

Experienced veterinarians should be also available on site. None of the procedures outlined will subject rabbits to significant discomfort, distress, pain, or injury. Should any abnormal events occur resulting in distress to any animal, it should be killed immediately in accordance with accepted guidelines such as the University of Kentucky IACUC. At the end of each experiment, each rabbit should be killed also in accordance with such directives.

The foregoing description of the invention was presented for purposes of illustration and description. It is not intended to be exhaustive or to limit the invention to the precise form disclosed. Obvious modifications or variations are contemplated in light of the above which provide illustrations describing the principles of the invention and its practical application to thereby enable one of ordinary skill in the art to utilize the invention in various ways as is suited for particular applications. All such modifications and variations fall within the true spirit and scope of the invention.

What is claimed is:

1. A method for detecting a fibrous cap in a blood vessel wall, the method comprising
   (a) illuminating the blood vessel wall with near-infrared light at a range of wavelengths from about 1200 to 2400 nm;
   (b) detecting light reflected from the blood vessel wall having a range of wavelengths from about 1200 to 2400 nm to obtain a sample reflectance spectrum; and
   (c) comparing the sample reflectance spectrum to a known reflectance spectrum of a fibrous cap as set forth in FIG. 3, wherein a sample reflectance spectrum that substantially matches the known reflectance spectrum of a fibrous cap indicates the presence of a fibrous cap in the blood vessel wall.

2. The method of claim 1, wherein the comparing is done using analytical software.

3. The method of claim 1, wherein the comparing is done using pattern recognition software.

4. The method of claim 1, wherein the sample spectrum is normalized by subtraction of a mean absorbance at each wavelength at each pixel to obtain a subtraction spectrum, and dividing the subtraction spectrum by a standard deviation of absorbances of each wavelength.

5. The method of claim 1, wherein the blood vessel wall is in vivo.

6. The method of claim 1, wherein the blood vessel is an artery.

7. The method of claim 1, wherein the blood vessel is a coronary artery.

8. A method of detecting a vulnerable plaque in a blood vessel wall, the method comprising
   locating a fibrous cap in a blood vessel wall by the method of claim 11; and
   determining the thickness of the fibrous cap based on the sample reflectance spectrum, wherein the presence of a fibrous cap that is less than 65 microns in thickness indicates that the blood vessel wall contains a vulnerable plaque.

9. A method for detecting cholesterol in a blood vessel wall, the method comprising
   (a) illuminating the blood vessel wall with near-infrared light at a range of wavelengths from about 1200 to 2400 nm;
   (b) detecting light reflected from the blood vessel wall having a range of wavelengths from about 1200 to 2400 nm to obtain a sample reflectance spectrum; and
   (c) comparing the sample reflectance spectrum to a known reflectance spectrum of cholesterol as set forth in FIG. 1, wherein a sample reflectance spectrum that substantially matches the known reflectance spectrum of cholesterol indicates the presence of cholesterol in the blood vessel wall.

10. The method of claim 9, wherein the blood vessel is a coronary artery.

11. A method for detecting lysophosphatidylcholine (LPC) in a blood vessel wall, the method comprising
    (a) illuminating the blood vessel wall with near-infrared light at a range of wavelengths from about 1200 to 2400 nm;
    (b) detecting light reflected from the blood vessel wall having a range of wavelengths from about 1200 to 2400 nm to obtain a sample reflectance spectrum; and
    (c) comparing the sample reflectance spectrum to a known reflectance spectrum of LPC as set forth in FIG. 2, wherein a sample reflectance spectrum that substantially matches the known reflectance spectrum of LPC indicates the presence of LPC in the blood vessel wall.

12. The method of claim 11, wherein the blood vessel is a coronary artery.

13. A method for detecting a lipid pool in a blood vessel wall, the method comprising
    (a) illuminating the blood vessel wall with near-infrared light at a range of wavelengths from about 1200 to 2400 nm;
    (b) detecting light reflected from the blood vessel wall having a range of wavelengths from about 1200 to 2400 nm to obtain a sample reflectance spectrum; and
    (c) comparing the sample reflectance spectrum to a known reflectance spectrum of a lipid pool as set forth in FIG. 12, wherein a sample reflectance spectrum that substantially matches the known reflectance spectrum of a lipid pool indicates the presence of a lipid pool in the blood vessel wall.

14. The method of claim 13, wherein the blood vessel is a coronary artery.

15. A method of determining whether a plaque containing a lipid pool in a blood vessel wall is vulnerable to rupture, the method comprising
    locating a lipid pool in a blood vessel wall by the method of claim 13; and
    determining the cross-sectional area of the lipid pool as a percentage of a total cross-sectional area of a plaque associated with the lipid pool; wherein a lipid pool greater than 30 percent of the total plaque indicates that the plaque is vulnerable to rupture.

* * * * *

UNITED STATES PATENT AND TRADEMARK OFFICE
CERTIFICATE OF CORRECTION

PATENT NO. : 6,816,743 B2
DATED : November 9, 2004
INVENTOR(S) : Moreno et al.

It is certified that error appears in the above-identified patent and that said Letters Patent is hereby corrected as shown below:

<u>Title page,</u>
Item [*] Notice, please delete info and add:
-- Subject to any disclaimer, the term of this patent is extended or adjusted under 1.705(c) by 509 days --.

Signed and Sealed this

Fifteenth Day of November, 2005

JON W. DUDAS
*Director of the United States Patent and Trademark Office*